United States Patent
Crocker et al.

(12) 
(10) Patent No.: US 6,432,952 B1
(45) Date of Patent: Aug. 13, 2002

(54) POLYMORPHIC FORM OF A TACHYKININ RECEPTOR ANTAGONIST

(75) Inventors: Louis Crocker, Belle Mead; Dongwei Cai, Edison; Jiang Wang, Bridgewater, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/697,405

(22) Filed: Oct. 26, 2000

Related U.S. Application Data

(60) Provisional application No. 60/162,711, filed on Oct. 29, 1999.

(51) Int. Cl.$^7$ .................. A61K 31/5377; A61P 25/24; C07D 413/06
(52) U.S. Cl. ..................... 514/236.2; 544/132
(58) Field of Search ................. 544/132; 514/236.2

(56) References Cited

U.S. PATENT DOCUMENTS 5,612,337 A    3/1997   Baker et al.

FOREIGN PATENT DOCUMENTS

WO    WO 99 01444    1/1999

*Primary Examiner*—Robert W. Ramsuer
(74) *Attorney, Agent, or Firm*—J. Eric Thies; Melvin Winokur

(57) ABSTRACT

This invention is concerned with a novel polymorphic forms of the compound 2-(R)-(1-(R)-(3,5-bis(trifluoromethyl) phenyl)ethoxy)4-( 5-(dimethyl-amino)methyl-1,2,3-triazol-4-yl)methyl-3-(S)-(4-fluorophenyl)morpholine hydrochloride which is a tachykinin receptor antagonist useful in the treatment or prevention of disorders of the central nervous system, inflammatory diseases, pain or migraine, asthma, and emesis. The instant polymorphic forms have advantages over the other known forms of 2-(R)-(1-(R)-(3,5-bis (trifluoromethyl)phenyl)ethoxy)4-( 5-(dimethylamino) methyl-1,2,3-triazol-4-yl)methyl-3-(S)-(4-fluorophenyl) morpholine hydrochloride in terms of thermodynamic stability and suitability for inclusion in pharmaceutical formulations.

14 Claims, 2 Drawing Sheets

POLYMORPHIC FORM OF A TACHYKININ RECEPTOR ANTAGONIST

This application claims the benefit of U.S. Provisional Application No. 60/162,711 filed Oct. 29, 1999.

SUMMARY OF THE INVENTION

This invention is concerned with novel polymorphic forms of the compound: 2-(R)-(1-(R)-(3,5-bis (trifluoromethyl)phenyl)ethoxy)-4-(5-(dimethyl-amino) methyl-1,2,3-triazol-4-yl)methyl-3-(S)-(4-fluorophenyl) morpholine hydrochloride. The present invention is also concerned with pharmaceutical formulations comprising the novel polymorphic forms of the compound as an active ingredient and the use of the compound and its formulations in the treatment of certain disorders.

The novel polymorphic forms of this invention are tachykinin receptor antagonists useful in the in the treatment or prevention of inflammatory diseases, emesis, depresssion, anxiety, and other neuropsychiatric diseases, including bipolar disorder and schizophrenia.

These polymorphic forms have advantages over the other known forms of 2-(R)-(1-(R)-(3,5-bis(tiifluoromethyl) phenyl)ethoxy)-4-(5-(dimethylanino)methyl-1,2,3-triazol-4-yl)methyl-3-(S)-(4-fluorophenyl)morpholine hydrochloride in terms of thermodynamic stability and suitability for inclusion in pharmaceutical formulations.

BACKGROUND OF THE INVENTION

The neuropeptide receptors for substance P (neurokinin-1; NK-1) are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition. Substance P (also called "SP" herein) is a naturally occurring undecapeptide belonging to the tachykinin family of peptides, the latter being so-named because of their prompt contractile action on extravascular smooth muscle tissue. In addition to SP the known mammalian tachykinins include neurokinin A and neurokinin B. The current nonmenclature designates the receptors for SP, neurokinin A, and neurokinin B as NK-1, NK-2, and NK-3, respectively.

Attempts have been made to provide antagonists for the receptors of substance P and other tachykinin peptides in order to more effectively treat the various disorders and diseases. In particular, U.S. Pat. No. 5,612,337, Example 12, Method B, discloses the compound 2-(R)-(1-(R)-(3,5-bis (trifluoromethyl)phenyl)-ethoxy)-4-(5-(dimethyl-amino) methyl-1,2,3-triazol-4-yl)methyl-3-(S)-(4-fluoro-phenyl) morpholine hydrochloride which has the structure:

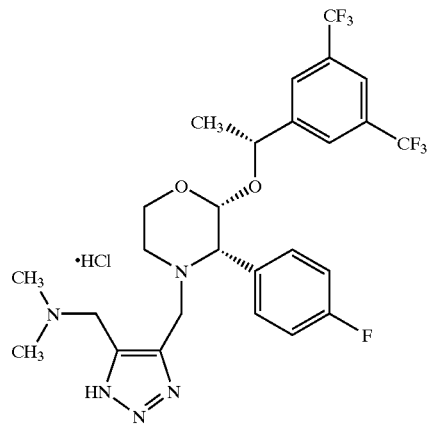

Morphological forms of pharmaceutical compounds may be of interest to those involved in the development of a suitable dosage form because if the morphological form is not held constant during clinical and stability studies, the exact dosage used or measured may not be comparable from one lot to the next. Once a pharmaceutical compound is produces for use, it is important to recognize the morphological form delivered in each dosage form to assure that the production process use the same form and that the same amount of drug is included in each dosage. Therefore, it is imperative to assure that either a single morphological form or some known combination of morphological forms is present. In addition, certain morphological forms may exhibit enhanced thermodynamic stability and may be more suitable than other morphological forms for inclusion in pharmaceutical formulations. As used herein, a polymorphic form of a chemical compound is the same chemical entity, but in a different crystalline arrangement.

DETAILED DESCRIPTION OF THE INVENTION

Figure 1:
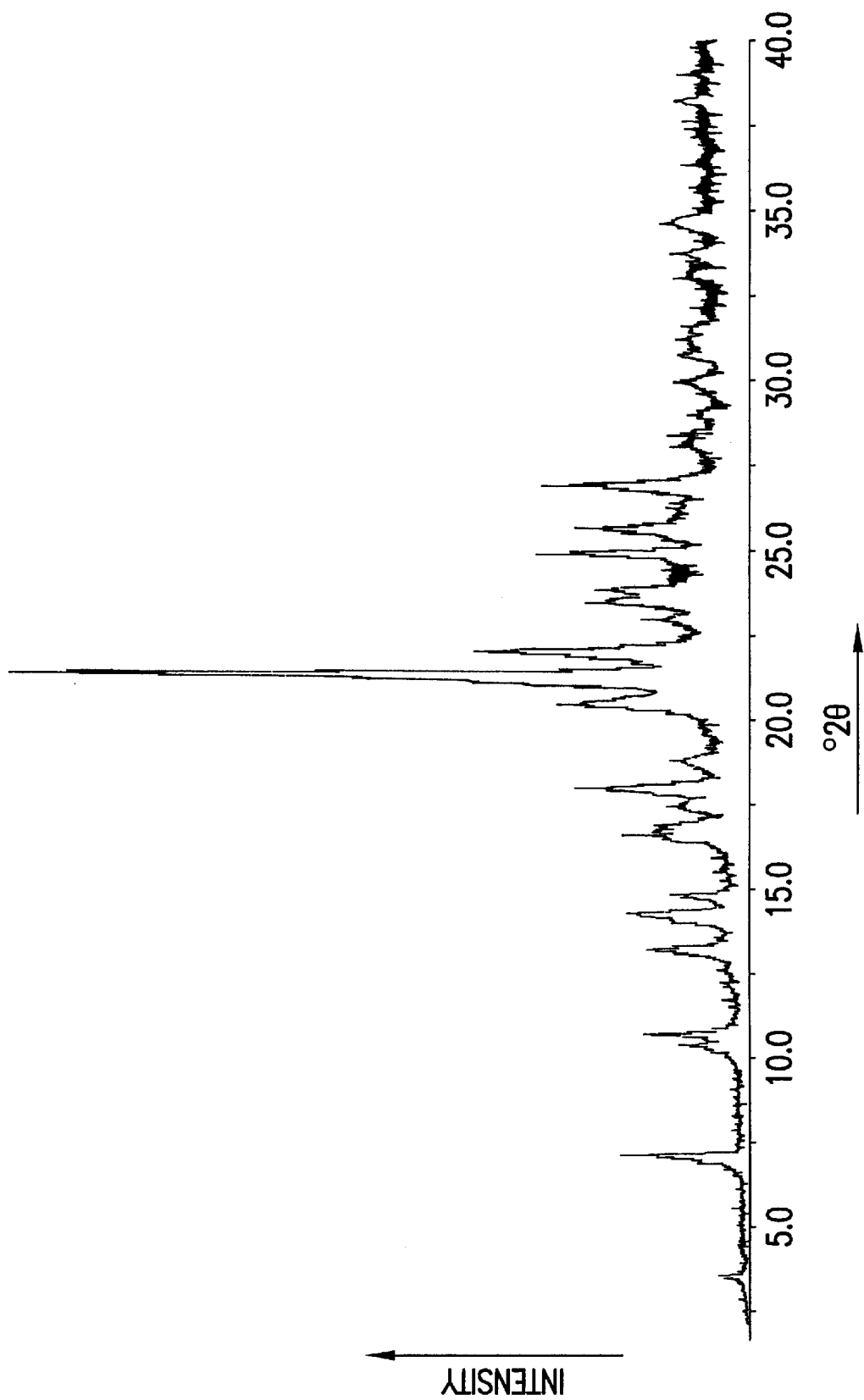
FIG. 1 is an X-ray powder diffraction pattern of Form I of 2-(R)-(1-(R)-(3 ,5-bis(trifluoromethyl)phenyl)ethoxy)-4-(5-(dimethylamino)methyl-1,2,3-triazol-4-yl)methyl-3-(S)-(4-fluorophenyl)morpholine hydrochloride.

The present invention is directed to polymorphic forms of the compound 2-(R)-(1-(R)-(3,5-bis(trifluoromethyl) phenyl)ethoxy)-4-(5-(dimethyl-amino)methyl-1,2,3-triazol-4-yl)methyl-3-(S)-(4-fluorophenyl)morpholine hydrochloride and the process for the preparation of these polymorphic forms.

The compound 2-(R)-(1-(R)-(3,5-bis(trifluoromethyl) phenyl)ethoxy)-4-(5-(dimethylamino)methyl-1,2,3-triazol-4-yl)methyl-3-(S)-(4-fluorophenyl)-morpholine hydrochloride has the structure:

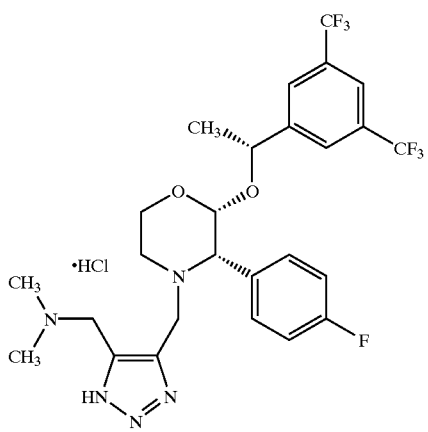

and is a tachykinin receptor antagonist useful in the treatment of inflammatory diseases, pain or migraine, asthma, and emesis.

The present invention is directed to a polymorphic form of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine hydrochloride which is designated Form I.

The present invention is further directed to a polymorphic form of 2-(R)-(1-(R)-(3,5-bis(trifluoromethyl)phenyl)ethoxy)4-(5-(dimethylamino)methyl-1,2,3-triazol-4-yl)methyl-3-(S)-(4-fluorophenyl)morpholine hydrochloride which is designated Form II.

The present invention is also directed to a polymorphic form of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine hydrochloride designated Form I which is substantially free of a polymorphic form of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine hydrochloride designated Form II.

The present invention is also directed to morphologically homogeneous 2-(R)-(1-(R)-(3,5-bis(trifluoromethyl)-phenyl)ethoxy)-4-(5-(dimethylamino)methyl-1,2,3-triazol-4-yl)methyl-3-(S)-(4-fluorophenyl)morpholine hydrochloride of Form I or Form II.

These particular polymorphic forms (herein designated "Form I" and "Form II") have superior properties over other crystalline forms of the compound in that it is thermodynamically more stable than other morphological forms and is more suitable for inclusion in pharmaceutical formulations.

The present invention is also concerned with a process for the preparation of Form I of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine hydrochloride which comprises:

adding anhydrous hydrogen chloride in an polar solvent such as isopropanol to a solution of 2-(R)-(1-(R)-(3,5-bis(trifluoromethyl)-phenyl)ethoxy)-4-(5-(dimethylamino)methyl-1,2,3-triazol-4-yl)methyl-3-(S)-(4-fluorophenyl)-morpholine in second polar solvent such as ethyl acetate, followed by addition of an antisolvent such as heptane to give Form I of 2-(R)-(1-(R)-(3,5-bis(trifluoromethyl)phenyl)ethoxy)4-(5-(dimethylamino)methyl-1,2,3-triazol-4-yl)methyl-3-(S)-(4-fluorophenyl)morpholine hydrochloride.

In addition, the present invention is concerned with an alternative process particularly useful for the preparation of Form I of 2-(R)-(1-(R)-(3,5-bis(trifluoromethyl)phenyl)ethoxy)-4-(5-(dimethylamino)methyl-1,2,3-triazol4-yl)methyl-3-(S)-(4-fluorophenyl)morpholine hydrochloride on a larger scale comprising:

suspending 2-(R)-(1-(R)-(3,5-bis(trifluoromethyl)phenyl)ethoxy)4-(5-(dimethylamino)methyl-1,2,3-triazol-4-yl)methyl-3-(S)-(4-fluorophenyl)morpholine hydrochloride of optional morphological composition in solution of ethyl acetate:isopropanol:heptane;

adding seed crystals of Form I of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine hydrochloride;

stirring the resultant mixture at about 0–50° C. for a period sufficient to result in the formation of Form I of 2-(R)-(1-(R)-(3,5-bis(trifluoromethyl)phenyl)-ethoxy)-4-(5-(dimethylamino)methyl-1,2,3-triazol-4-yl)methyl-3-(S)-(4-fluorophenyl)morpholine hydrochloride.

In the processes for the preparation of Form I of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine hydrochloride to optimize the formation of Form I it is preferred that the concentration of 2-(R)-(1-(R)-(3,5-bis(trifluoro-methyl)-phenyl)ethoxy)-4-(5-(dimethylamino)methyl-1,2,3-triazol-4-yl)methyl-3-(S)(4-fluorophenyl)morpholine hydrochloride in the solution should be maintained below the solubility of Form II. Because the nucleation and growth rates of Form II are much faster than Form I, even a small degree of supersaturation of Form II may result in its nucleation and crystal formation.

In the processes for the preparation of Form I of 2-(R)-(1-(R)-(3,5-bis(trifluoromethyl)phenyl)ethoxy)4-(5-(dimethylamino)methyl-1,2,3-triazol-4-yl)methyl-3-(S)-(4-fluorophenyl)morpholine hydrochloride it is preferred that the ratio of isopropanol:ethyl acetate is 1:1 to 1:100 (v:v) and it is morepreferred that the ratio of isopropanol:ethyl acetate is 1:5 to 1:50 (v:v) and it is still more preferred that the ration of isopropanol:ethyl acetate is about 1:10 (v:v).

In the processes for the preparation of Form I of 2-R)-(1-(R)-(3,5-bis(trifluoromethyl)p henyl)ethoxy)-4-(5-(dimethylamino)methyl-1,2,3-triazol-4-yl)methyl-3-(S)-(4-fluorophenyl)morpholine hydrochloride it is preferred that water be present in the solvent system to optimlze the formation of Form I of 2-(R)-(1-(R)-(3,5-bis(trifluoromethyl)phenyl)-ethoxy)-4-(5-(dimethyl-amino)methyl 1,2,3-triazol-4-yl)methyl-3-(S)-(4-fluorophenyl)morpholine hydrochloride. In the solvent system it is preferred that water be present at about 100–10,000 mg/L, as reflected by Karl-Fisher titration. In the solvent system it is even more preferred that water be present at about 1000–5000 mg/L, as reflected by Karl-Fisher titration. In the solvent system it is still more preferred that water be present at about 2000±100 mg/L, as reflected by Karl-Fisher titration.

In the processes for the preparation of Form I of 2-)-(1-(R)-(3,5-bis(trifluoromethyl)phenyl)ethoxy)-4-(5-(dimethylamino )methyl-1,2,3-triazol- 4-yl)methyl-3-(S)-(4-fluorophenyl)morpholine hydrochloride it is preferred that the ratio of the antisolvent (heptane):polar solvents (isopropanol:ethyl acetate) is 10:1 to 1:1, more preferably about 5:1 to 1.5:1, still more preferably about 2:1, and even more preferably about 2.33:1.

In the processes for the preparation of Form I of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine hydrochloride it is preferred that the antisolvent heptane is added to the polar solvents as three separate charges. It is preferred that the first charge of antisolvent be prior to addition of seed crystals (and optionally may be made at a fast rate of addition). It is preferred that the ratio of polar solvents:antisolvent after the first charge of antisolvent be about 5:1 to 3:1 and more preferably about 4:1. After addition of the first charge of antisolvent it is preferred that the mixture be aged for about 1 hour. It is preferred that the second charge of antisolvent be added after seeding and at a slow rate of addition. It is preferred that the second charge of antisolvent be added over a period of 1–10 hours, more preferably over a period of 3–6 hours and even more preferably over a period of about 4.5±0.5 hours. It is preferred that the ratio of polar solvents:antisolvent after the second charge of antisolvent be about 2:1 to 1:2 and more preferably about 1:1. After addition of the second charge of antisolvent it is preferred that the mixture be aged for about 0.5–1 hour. It is preferred that the third charge of antisolvent be after the second charge (and optionally may be made at a fast rate of addition). It is preferred that the third charge of antisolvent be added over a period of 0–5 hours, more preferably over a period of 0.5–3 hours and even more preferably over a period of about 1–1.5 hours. It is preferred that the ratio of polar solvents:antisolvent after the third charge of antisolvent be about 1:1 to 1:10 and more preferably about 3:7. After addition of the third charge of antisolvent it is preferred that the mixture be aged for a period of 0.5–5 hours, and more preferably for a period of about 2±0.5 hours.

In the processes for the preparation of Form I of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine hydrochloride it is preferred that the ratio of isopropanol:ethyl acetate:heptane is 0.1–1.0 mL:1–10 mL:10–20 mL per gram of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine. In these process it is more preferred that the ratio of isopropanol:ethyl acetate:heptane is 0.5 mL:5 mL:16.5 mL per gram of 2-(R)-(1-(R)-(3,5-bis(trifluoromethyl)phenyl)ethoxy)-4-(5-(dimethyl-amino)methyl-1,2,3-triazol-4-yl)methyl-3-(S)-(4-fluorophenyl)morpholine.

In the processes for the preparation of Form I of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine hydrochloride it is preferred that the initial concentration of 2-(R)-(1-(R)-(3,5-bis(trifluoromethyl)phenyl)ethoxy)-4-(5-(dimethylarnino)methyl-1,2,3-triazol-4-yl)methyl-3-(S)-(4-fluorophenyl)morpholine hydrochloride is about 10–1000 g/L, more preferably 50–500 g/L, even more preferably 100–250 g/L and still more preferably about 180±10 g/L.

In the processes for the preparation of Form I of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine hydrochloride it is preferred that the particle size of the seed of Form I of 2-(R)-(1-(R)-(3,5-bis(trifluoromethyl)phenyl)-ethoxy)-4-(5-(dimethylamino)methyl-1,2,3-triazol-4-yl)methyl-3-(S)-(4-fluoro-phenyl)morpholine hydrochloride is less than about 500 $\mu$m mean average particle diameter, more preferably less than about 200 $\mu$m mean average particle diameter, even more preferably less than about 100 $\mu$m mean average particle diameter, and still more preferably about 20 $\mu$m mean average particle diameter.

To maximize the consistency of particle size distribution of Form I of 2-(R)-(1-(R)-(3,5-bis(trifluoromethyl)phenyl) ethoxy)-4-(5-(dimethylamino)methyl-1,2,3-triazol-4-yl) methyl-3-(S)-(4-fluorophenyl)morpholine hydrochloride it is preferred that a consistent seed size or size distribution is employed.

In the processes for the preparation of Form I of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine hydrochloride it is preferred that the loading of the seed of Form I of 2-(R)-(1-(R)-(3,5-bis (trifluoromethyl)phenyl)-ethoxy)-4-(5-(dimethylamino) methyl-1,2,3-triazol-4-yl)methyl-3-(S)-(4-fluorophenyl) morpholine hydrochloride be 1–10 wt % and more preferably about 5 wt %.

The present invention is further concerned with a process for the preparation of Form II of 2-(R)-(1-(R)-(3,5-bis (trifluoromethyl)phenyl)ethoxy)-4-(5-(dimethylamino) methyl-1,2,3-triazol-4-yl)methyl-3-(S)-(4-fluorophenyl) morpholine hydrochloride which comprises:

adding anhydrous hydrogen chloride in diethyl ether to a solution of 2-(R)-(1-(R)-(3,5-bis(tfluoromethyl)-phenyl) ethoxy)-4-(5-(dimethylamino)methyl- 1,2,3-triazol-4-yl) methyl-3-(S)-(4-fluorophenyl)morpholine in methyl tert-butyl ether to give Form II of 2-(R)-(1-(R)-(3,5-bis (trifluoromethyl)phenyl)ethoxy)-4-(5-(dimethylamino) methyl-1,2,3-triazol-4-yl)methyl-3-(S)-(4-fluorophenyl) morpholine hydrochloride.

Similarly, the present invention is also directed to a process for the preparation of morphologically homogeneous 2-(R)-(1-(R)-(3,5-bis(trifluoromethyl)-phenyl) ethoxy)-4-(5-(dimethylamino)methyl-1,2,3-triazol-4-yl) methyl-3-(S)-(4-fluorophenyl)morpholine hydrochloride, comprising any of the aforementioned processes.

The compound of this invention, the novel polymorphic forms of 2-(R)-(1-(R)-(3,5-bis(trifluoromethyl)phenyl) ethoxy)-4-(5-(dimethylarnino)methyl-1,2,3-triazol-4-yl) methyl-3-(S)-(4-fluorophenyl)morpholine hydrochloride, is a tachykinin receptor antagonists useful in the treatment of inflammatory diseases, pain or migraine, asthma, and emesis. Accordingly, the present invention is further concerned with pharmaceutical formulations comprising this polymorphic form as an active ingredient, and the use of this polymorphic form and its formulations in the treatment of certain disorders.

Form I of 2-(R)-(1-(R)-(3,5-bis(trifluoromethyl)phenyl) ethoxy)-4-(5-(dimethylamino)methyl-1,2,3-triazol-4-yl) methyl-3-(S)-(4-fluorophenyl)morpholine hydrochloride an anhydrous crystalline material and exhibits a high degree of thermal stability as a neat solid. Form I is thermodynamically more stable than Form II.

Form II of 2-(R)-(1-(R)-(3,5-bis(trifluoromethyl)phenyl) ethoxy)-4-(5-(dimethylamino)methyl-1,2,3-triazol-4-yl) methyl-3-(S)-(4-fluorophenyl)morpholine hydrochloride is an anhydrous crystalline material melting at 254° C. which is obtained directly from recrystallization in the chemical synthesis of 2-(R)-(1-(R)-(3,5-bis(trifluoromethyl)phenyl) ethoxy)-4-(5-(dimethyl-amino)methyl-1,2,3-triazol-4-yl) methyl-3-(S)-(4-fluorophenyl)morpholine hydrochloride.

X-Ray Powder Diffraction (XRPD)

Figure 2:
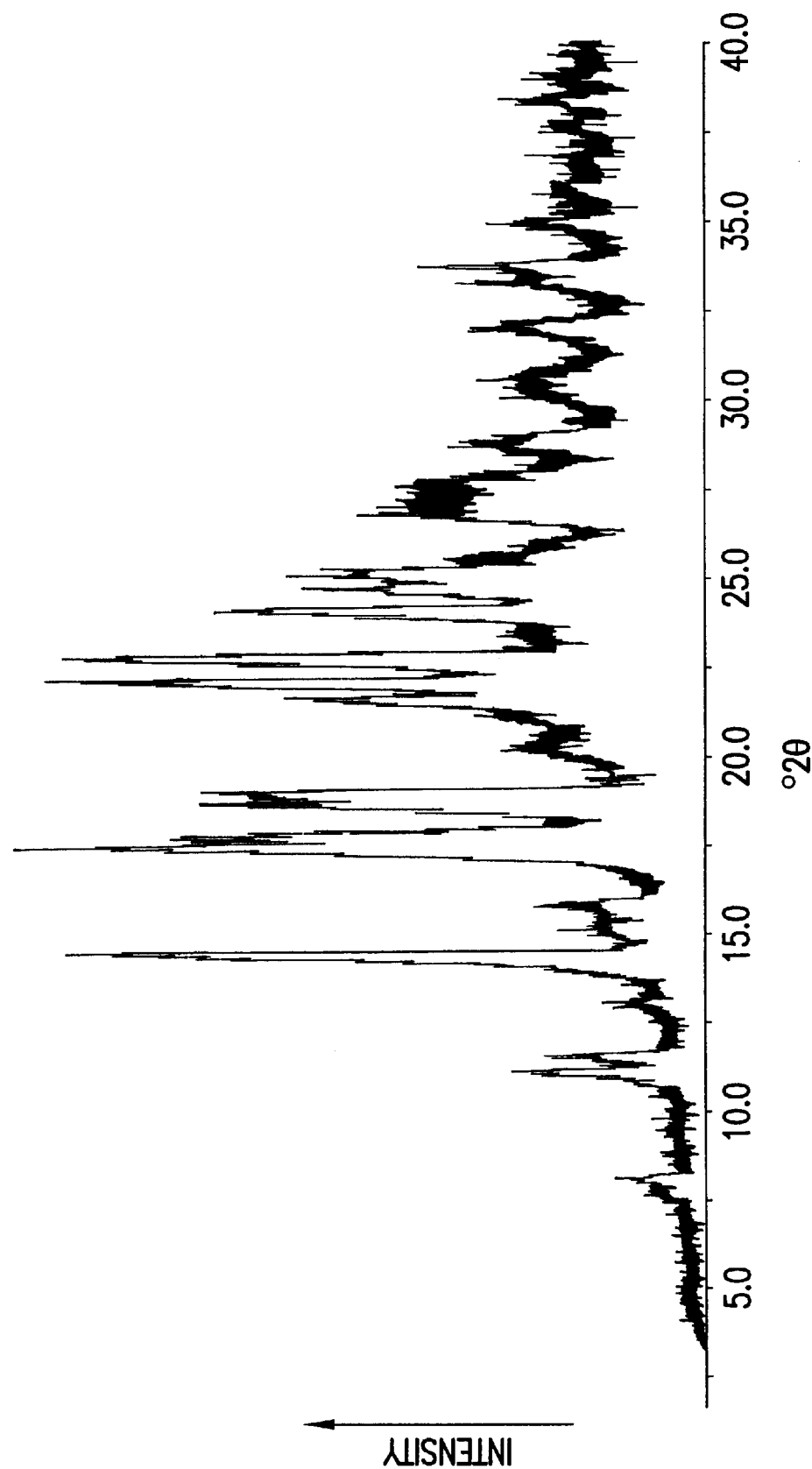
FIG. 2 is an X-ray powder diffraction pattern of Form II of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine hydrochloride.

X-Ray powder diffraction studies have been widely used to elucidate molecular structures, crystallinity and polymorphism. X-ray powder diffraction (XRPD) patterns were recorded using a Philips-model APD 3720 powder diffractometer equipped with a 3 kw X-ray generator (CuKa1 radiation) and a NaI (Ti) scintillation detector. Measurements were made from 3° to 45° (2 theta) with the sample maintained at ambient room temperature and are presented in FIG. 1 and FIG. 2. Form I of 2-(R)-(1-(R)-(3,5-bis (trifluoromethyl)phenyl)ethoxy)-4-(5-(dimethylamino) methyl-1,2,3-triazol-4-yl)methyl-3-(S)-(4-fluorophenyl) morpholine hydrochloride was characterized by an X-ray powder diffraction pattern with key reflections at approximately: 7.0, 10.6, 13.1, 14.1, 16.4, 17.9, 20.4, 21.3, 22.0, 23.8, 24.8, 25.6, and 26.9° (2 theta). Form II of 2-(R)-(1-(R)-(3,5-bis(trifluoromethyl)-phenyl)ethoxy)-4-(5-(dimethylamino)methyl-1,2,3-triazol-4-yl)methyl-3-(S)-(4-fluorophenyl)morpholine hydrochloride was characterized by an X-ray powder diffraction pattern with key reflections at approximately: 10.0, 10.5, 13.3, 16.4, 16.7, 17.7, 18.0, 19.3, 20.7, 21.1, 21.8, 23.2, 23.8, 24.5, 26.0, 27.0, 28.1, 28.4, 30.0, 31.5, 32.8, and 33.3° (2 theta). These XRPD patterns confirm that both samples are distinct crystalline forms. Both Form I and Form II exhibit intense peaks characteristic of crystalline material.

Differential Scanning Calorimeteric Cell [DSC]

Differential scanning calorimetry (10° C./min in nitrogen atmosphere) of Form I of 2-(R)-(1-(R)-(3,5-bis (trifluoromethyl)phenyl)ethoxy)-4-(5-(dimethyl-amino) methyl-1,2,3-triazol-4-yl)methyl-3-(S)-(4-fluorophenyl) morpholine hydrochloride and of Form It of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)-morpholine hydrochloride showed differences in their thermal behavior.

In particular, the DSC curve of Form I of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine hydrochloride exhibited a transition endotherm at 62° C. (peak temperature) with an extrapolated onset temperature of 58° C. and an enthalpy of 6.0 J/g, and a melting-decomposition endotherm at about 201° C. (peak temperature) with an extrapolated onset temperature of 198° C. and an enthalpy of 49.1 J/g.

The DSC curve of Form II of 2-(R)-(1-(R)-(3,5-bis (trifluoromethyl)-phenyl)ethoxy)4-(5-(dimethylamino) methyl-1,2,3-triazol-4-yl)methyl-3-(S)-(4-fluorophenyl) morpholine hydrochloride exhibited a transition endotherm at 115° C. (peak temperature) with an extrapolated onset temperature of 108° C. and an enthalpy of 5.0 J/g, and a melting-decomposition endotherm at about 203° C. (peak temperature) with an extrapolated onset temperature of 200° C. and an enthalpy of 47.3 J/g.

NMR Proton and carbon nuclear magnetic resonance spectra on Form I and Form II indicated no chemical change in the compound in the conversion from Form II to Form I.

Solubility The solubility of Form I of 2-(R)-(1-(R)-(3,5-bis (trifluoromethyl)-phenyl)ethoxy)-4-(5-(dimethylamino) methyl-1,2,3-triazol-4-yl)methyl-3-(S)-(4-fluorophenyl) morpholine hydrochloride in isopropyl acetate at 25° C. was determined to be 7.4±0.3 mg/ml. The solubility of Form I of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine hydrochloride in isopropyl acetate at 25° C. was determined to be 10.9±1.1 mg/ml. The ratio of the solubilities indicates that Form I is more thermodynamically stable than Form II by approximately 0.2 kcal/mol at this temperature.

TACHYKININ ANTAGONISM ASSAY

The compound of this invention, the polymorphic Forms I and II of 2-(R)-(1-(R)-(3,5-bis(trifluoromethyl)phenyl) ethoxy)-4-(5-(dimethylamino)methyl-1,2,3-triazol-4-yl) methyl-3-(S)-(4-fluorophenyl)morpholine hydrochloride, is useful for antagonizing tachykinins, in particular substance P and neurokinin A in the treatment of gastrointestinal disorders, central nervous system disorders, inflammatory diseases, pain or migraine, asthma, and emesis in a mammal in need of such treatment. This activity may be demonstrated by the following assay.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 MM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serurn, 2 mM glutamine, 100U/ml penicillin-streptomycin, and 90% DMEM media (GIBCO, Grand Island, N.Y.) in 5% $CO_2$ at 37° C. for three days before the binding assay.

B. Stable Expression in CHO

To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer suplemented with 0.625 mg/ml Herring sperm DNA at 300 V and 950 uF using the EBI GENEZAPPER (EBI). The transfected cells were incubated in CHO media [10 % fetal calf serum, 100 U/ml pennicilin-streptomycin, 2 mM glutamine, 1/500 hypoxanthine-thymidine (ATCC), 90% I1DM media (JRH BIOSCIENCES, Lenexa, KS), 0.7 mg/mI G418 (GIBCO)] in 5% $CO_2$ at 37° C. until colonies were visible. Each colony was separated and propagated. The cell clone with the highest number of human NK1R was selected for subsequent applications such as drug screening.

C . Assay Protocol using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM MnCl2, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}$I-SP binding (approximately 50,000 to 200, 000 cells). In the binding assay, 200 ul of cells were added to a tube containing 20 ul of 1.5 to 2.5 nM of $^{125}$I-SP and 20 ul of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1 % polyethylenimine. The filter was washed with 3 ml of wash buffer (50 mM Tris pH 7.5, 5 mM $MnCl_2$, 150 mM NaCl) three times and its radioactivity was determined by gamma counter.

The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1 N HCl is added. Each well is sonicated at 4° C. and extracted with CHCl$_3$/methanol (1:1). The aqueous phase is applied to a 1 ml Dowex AG 1X8 ion exchange column. The column is washed with 0.1 N formic acid followed by 0.025 M ammonium formate-0.1 N formic acid. The inositol monophosphate is eluted with 0.2 M ammonium formate-0.1 N formic acid and quantitated by beta counter.

The activity of the present compound may also be demonstrated by the assay disclosed by Lei, et al., *British J. Pharmacol.*, 105, 261–262 (1992).

The compound of the present invention is of value in the treatment of a wide variety of clinical conditions which are characterized by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to MV disease, head trauma, Parkinson's disease, Huntington's disease, Pick's disease, Creutzfeldt-Jakob disease, or due to multiple aetiologies; Parkinson's disease and other extrapyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; sleep disorders and sleep disturbances, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus and restless legs and non specific REM disturbances as seen in ageing; disorders benefited by improving sleep quality or increasing sleep efficiency and augmenting sleep maintenance; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compound of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve-disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compound of the present invention is also of value in the treatment of a combination of the above conditions, in particular in the treatment of combined post-operative pain and post-operative nausea and vomiting.

The compound of the present invention is particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compound of the present invention is of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyriridine antagonists; mitotic inhibitors, for example, vinca alkaloids and derivatives of podophyllotoxin; and cytotoxic antibiotics.

Particular examples of chemotherapeutic agents are described, for example, by D. J. Stewart in "Nausea and Vomiting: Recent Research and Clinical Advances", Eds. J. Kucharczyk, et al., CRC Press Inc., Boca Raton, Fla., USA (1991), pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, and chlorambucil [R. J. Gralla, et al., *Cancer Treatment Reports*, 68(1), 163–172 (1984)].

The compound of the present invention is also of use in the treatment of emesis induced by radiation including radiation therapy such as in the treatment of cancer, or radiation sickness; and in the treatment of post-operative nausea and vomiting.

For the treatment of certain conditions it may be desirable to employ the compound of the present invention in conjunction with another pharmacologically active agent. It will be appreciated that the compound of the present invention may be presented together with another therapeutic agent as a combined preparation for simultaneous, separate or sequential use for the relief of emesis. Such combined preparations may be, for example, in the form of a twin pack.

A further aspect of the present invention comprises the compound of the present invention in combination with a 5-HT$_3$ antagonist, such as ondansetron, granisetron, tropisetron or zatisetron, or other anti-emetic medicaments, for example dexamethasone or a dopamine antagonist such as metoclopramide. Additionally, the compound of the present invention may be administered in combination with an anti-inflammatory corticosteroid, such as dexamethasone. Furthermore, the compound of the present invention may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. phannacol.*, (1993) 250, R5–R6, the compound of the present invention was found to attenuate the retching and vomiting induced by cisplatin.

The compound of the present invention is also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and headache, including migraine, acute or chronic tension headache, cluster headache, temporomandibular pain, and maxillary sinus pain. The present invention further provides the compound of the present invention for use in therapy.

According to a further or alternative aspect, the present invention provides compound of the present invention for use in the manufacture of a medicament for the treatment or prevention of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of the compound of the present invention or a composition comprising the compound of the present invention.

For the treatment of certain conditions it may be desirable to employ a compound according to the present invention in conjunction with another pharmacologically active agent. For example, for the treatment of respiratory diseases such as asthma, the compound of the present invention may be used in conjunction with a bronchodilator, such as a β$_2$-adrenergic receptor antagonist or tachykinin antagonist which acts at NK-2 receptors The compound of the present invention and the bronchodilator may be administered to a patient simultaneously, sequentially or in combination. For the treatment of conditions that require antagonism of both neurokinin-1 and neurokinin-2, including disorders associated with bronchoconstriction and/or plasma extravasation in airways, such as asthma, chronic bronchitis, airways disease, or cystic fibrosis, the compound of the present invention may be used in conjunction with a tachykinin antagonist which acts at neurokinin-2 receptors, or with tachykinin receptor antagonist which acts at both neurokinin-1 and neurokinin-2 receptors.

Likewise, the compound of the present invention may be employed with a leukotriene antagonists, such as a leukotriene D$_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of the compound of the present invention and an effective amount of a bronchodilator. The present invention also provides a composition comprising the compound of the present invention, a bronchodilator, and a pharmaceutically acceptable carrier.

It will be appreciated that for the treatment or prevention of migraine, the compound of the present invention may be used in conjunction with other anti-migraine agents, such as ergotamines or 5-HT$_1$ agonists, especially sumatriptan or rizatriptan. Likewise, for the treatment of behavioural hiyperalgesia, the compound of the present invention may be used in conjunction with an antagonist of N-methyl D-aspartate (NMDA), such as dizocilpine. For the treatment or prevention of inflammatory conditions in the lower urinary tract, especially cystitis, the compound of the present invention may be used in conjunction with an anti-inflammatory agent such as a bradykinin receptor antagonist. The present invention also provides a composition comprising the compound of the present invention, a bronchodilator, and a pharmaceutically acceptable carrier.

It will be appreciated that for the treatment or prevention of pain or nociception, the compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, afenantil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, afenantil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising the compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be further appreciated that for the treatment or prevention of depression and/or anxiety the compound of the present invention may be used in combination with an antidepressant agent or anti-anxiety agent. Suitable classes of antidepressant agents of use in the present invention include: norepinephrine reuptake inhibitors, selective serotonin include: norepinephrine reuptake inhibitors, selective serotonin reuptake inhibitors, monoamine oxidase inhibitors, reversible monoamine oxidase inhibitors, serotonin and noradrenaline reuptake inhibitors, corticotropin releasing factor (CRF) antagonists, a-adrenoreceptor antagonists and atypical antidepressants. Another class of antidepressant agent of use in the present invention are noradrenergic and specific serotonergic antidepressants, such as mirtazapine. Suitable examples of norepinephrine reuptake inhibitors include amitripdyline, clomipramine, doxepine, imipramine, trimipramine, amoxapine, desipramine, maprotiline, nortriptyline, reboxetine and protriptyline and pharmaceutically acceptable salts thereof. Suitable examples of selective serotonin reuptake inhibitors include fluoxetine, fluvoxarnine, paroxetine, and sertraline and pharmaceutically acceptable salts thereof. Suitable examples of monoamine oxidase inhibitors include isocarboxazid, phenelzine, tranylcypromain and selegiline, and pharmaceutically acceptable salts thereof. Suitable examples of reversible monoamine oxidase inhibitors include moclobemide, and pharmaceutically acceptable salts thereof. Suitable examples of serotonin and noradrenaline reuptake inhibitors include venlafaxine, and pharmaceutically acceptable salts thereof. Suitable examples of corticotropin releasing factor (CRF) antagonists include those compounds described in International Patent Specification Nos. WO 94/13643, WO 94/13644, WO 94/13661, WO 94/13676 and WO 94/13677. Suitable examples of atypical antidepressants include bupropion, lithium, nefazoedone, sibutramine, trazodone and viloxazine, and pharmaceutically acceptable salts thereof. Other antidepressants of use in the present invention include adinozolam, alaproclate, amineptine, amitryptyline/chlordiazepoxide combination, atipamezole, azamianserin, bazinaprine, fefuraline, bifemelane, binodaline, bipenamol, brofaromine, bupropion, caroxazone, cericlamine, cianopranine, cimoxatone, citaloprani, clemeprol, clovoxamine, dasepinil, deanol, demexiptiline, dibenzepin, dothiepin, droxidopa, enefexine, setazolam, etoperidone, femoxetine, fengabine, fezolamine, fluotracen, idazoxan, indalpine, indeloxazine, iprindole, levoprotiline, litoxetine, lofepramine, medifoxamine, metapramine, metralindole, mianserin, milnacipran, minaprine, mirtazapine, montirelin, nebracetam, nefopam, nialamide, nomifensine, norfluoxetine, orotirelin, oxaflozane, pinazepam, pirindole, pizotyline, ritaserin, rolipram, sercloremine, setiptiline, sibutramine, sulbutiamine, sulpride, teniloxazine, thozalinone, thymoliberin, tianeptine, tiflucarbine, tofenacin, tofisopam, toloxatone, tomoxetine, veralipride, viqualine, zimelidine, and zometapine, and pharmaceutically acceptable salts thereof, and St. John's wort herb, or *Hypericum peroratum*, or extracts thereof. Preferred antidepressant agents include selective serotonin reuptake inhibitors, in particular, fluoxetine, fluvoxamine, paroxetine, and sertraline and pharmaceutically acceptable salts thereof Suitable classes of anti-anxiety agents of use in the present invention include benzodiazepines and 5-HT1A agonists or antagonists, especially 5-HT$_{1A}$ partial agonists, and corticotropin releasing factor (CRF) antagonists. In addition to benzodiazepines, other suitable classes of anti-anziety agents are nonbenzodiazepine sedative-hypnotic drugs such as zolpidem; mood-stabilizing drugs such as clobazam, gabapentin, lamotrigine, loreclezole, oxcarbamazepine, stiripentol and vigabatrin; and barbituates. Suitable banzodiazepines of use in the present invention include alprazolam, chlordizepoxide, clonazepam, chIorazepate, diazepam, halazepam, lorezepam, oxazepam and prazepam, and pharmaceutically acceptable salts thereof. Suitable examples of 5-HT$_{1A}$ agonists or antagonists of use in the present invention include, in particular, the 5-HT$_{1A}$ partial agonists buspirone, flesinoxan, gepirone, ipsapirone and pindolol, and pharmaceutically acceptable salts thereof. Suitable examples of corticotropin releasing factor (CRF) antagonists include those compounds described in International Patent Specification Nos. WO 94/13643, WO 94/13644, WO 94/13661, WO 94/13676 and WO 94/13677. Another class of anti-anxiety agent of use in the present invention are compounds having muscarinic cholinergic activity. Suitable compounds in this class include m 1 muscarinic cholinergic receptor antagonists such as those compounds described in European Patent Specification Nos. 0 709 093, 0 709 094 and 0 773 021 and International Patent Specification No. WO 96/12711. Another class of anti-anxiety agent of use in the present invention are compounds acting on ion channels. Suitable compounds in this class include carbamazepine, lamotrigine and valproate, and pharmaceutically acceptable salts thereof.

Therefore, in a further aspect of the present invention, there is provided a pharmaceutical composition comprising the compound of the present invention and an antidepressant or an anti-anxiety agent, together with at least one pharmaceutically acceptable carrier or excipient.

Suitable antipsychotic agents of use in combination with the compound of the present invention include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. Suitable examples of dibenzazepines include clozapine and olanzapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with the compound of the present invention may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agnet of use in combination with the compound of the present invention include dopamine receptor antagonists, especially D2, D3 and D4 dopamine receptor antagonists, and muscarinic ml receptor agonists. An example of a D3 dopamine receptor antagonist is the compound PNU-99194A. An example of a D4 dopamine receptor antagonist is PNU-101387. An example of a muscarinic m1 receptor agonist is xanomeline.

Another class of antipsychotic agent of use in combination with the compound of the present invention is the 5-HT2A receptor antagonists, examples of which include MDL100907 and fananserin. Also of use in combination with the compound of the present invention are the serotonin dopamine antagonists (SDAs) which are believed to combine 5-HT2A and dopamine receptor antagonist activity, examples of which include olanzapine and ziperasidone.

Therefore, in a further aspect of the present invention, there is provided a pharmaceutical composition comprising the compound of the present invention and an antipsychotic agent, together with at least one pharmaceutically acceptable carrier or excipient.

The compound of the present invention and the other pharmacologically active agent may be administered to a patient simultaneously, sequentially or in combination. It will be appreciated that when using a combination of the present invention, the compound of the present invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The pharmacological profile of the compound of the present invention offers the opportunity for their use in therapy at low doses thereby minimizing the risk of unwanted side effects. The compound of this invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of a condition associated with an excess of tachykinins, an appropriate dosage level will generally be about 0.001 to 50 mg per kg patient body weight per day which may be administered in single or multiple doses. Preferably, the dosage level will be about 0.01 to about 25 mg/kg per day; more preferably about 0.05 to about 10 mg/kg per day. For example, in the treatment of conditions involving the neurotransmission of pain sensations, a suitable dosage level is about 0.001 to mg/kg per day, preferably about 0.005 to 10 mg/kg per day, and especially about 0.01 to 5 mg/kg per day. A compound may be administered on a regimen of 1 to 4 times per day, preferably once or twice per day. In the treatment or prevention of a disorder of the central nervous system, a suitable dosage level is about 0.01 to 5 mg/kg per day, preferably about 0.015 to 1.5 mg/kg per day, and especially about 0.3 to 1 mg/kg per day. In the treatment or prevention of a disorder of the central nervous system, a suitable dosage is about 1 to 100 mg per day, preferably about 5 to 50 mg per day, and especially about 20 to 40 mg per day. The compound may be administered on a regimen of 1 to 4 times per day, preferably once or twice per day.

It will be appreciated that the amount of the compound of the present invention required for use in any treatment will vary not only with the particular compounds or composition selected but also with the route of administration, the nature of the condition being treated, and the age and condition of the patient, and will ultimately be at the discretion of the attendant physician.

The pharmaceutical compositions of this invention may be used in the form of a pharmaceutical preparation, for example, in solid, semisolid or liquid form, which contains one or more of the compound of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention.

The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solution, suitably flavoured syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For the treatment of the clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrastemal injection or infusion-techniques.

Methods for preparing the polymorphic forms of this invention are illustrated in the following Examples. Many of the starting materials are either commercially available or known in the literature and others can be prepared following literature methods described for analogous compounds (such as in U.S. Pat. No. 5,612,337 and U.S. Pat. No. 5,719,147). The skills required in carrying out the reaction and purification of the resulting reaction products are known to those in the art. Purification procedures include crystallization, normal phase or reverse phase chromatography.

The following examples are provided for the purpose of further illustration only and are not intended to be limitations on the disclosed invention.

EXAMPLE 1

4-N,N-Dimethylaminomethyl-5-formyl-1,2,3-triazole

| Materials | Amount | Mol (equiv) | MW |
|---|---|---|---|
| 1-Dimethylamino-2-propyne | 16.65 g (12.85 mL) | 0.20 mol | 83.13 |
| n-Butyllithium (1.6 M in hexanes) | 125 mL | 0.20 mol | |
| N-Methylformanilide | 27.05 g or 24.7 mL | 0.20 mol | 135.17 |
| Trifluoroacetic acid | 22.80 g or 15.4 mL | 0.20 mol | 114.02 |
| Sodium azide | 12.35 g | 0.19 mol | 65.01 |
| THF | 200 mL | | |
| DMF | 500 mL | | |
| Water | 25 mL and 200 mL | | |
| MTBE | 600 mL | | |

1-Dimethylamino-2-propyne (16.65 g, 12.85 mL, 0.2 mol) was dissolved in TBF (200 mL) and the resulting yellow homogeneous solution was cooled in a dry ice-acetone bath. n-Butyllithium (1.6 M in hexanes, 125 mL, 0.2 mol) was added over ca. 5 minutes maintaining the temperature at −25 to −15° C. n-Butyllithium was titrated with N-pivaloyl-o-toluidine (*J. Org. Chem.* 1989, 54, 509.). After completion of the addition, the reaction mixture was white pasty (but stirrable) due to the aggregates of the acetylide at high concentration.

N-Methylformanilide (27.05 g, 24.7 mL, 0.2 mol) was added in one portion and the reaction mixture was allowed to warm to room temperature over ca. 15 minutes and further aged at this temperature for 30 minutes. The addition of N-Methylformanilide wasn't exothermic at −20° C. The reaction becomes clear homogeneous (slightly yellow) at around 0° C.

The reaction mixture was then cooled over a dry ice-acetone bath and trifluoroacetic acid TFA (22.80 g, 15.4 mL, 0.2 mol) was added over ca. 10 minutes maintaining the temperature below −30° C. The resulting acetylenic aldehyde was not stable for more than 1–2 hours at −30° C. (more stable at lower temperature). The reaction mixture was yellow and would turn to dark brown upon decomposition of the aldehyde. Crude acetylenic aldehyde must be quenched into sodium azide within 1 to 2 hours.

The reaction mixture (kept below −30° C.) was then added to a DMF solution (500 mL) containing sodium azide (12.35 g, 0.19 mol) and water (25 mL) at room temperature over ca. 15 minutes. Final temperature of the batch was ~18° C. The solution was orange-red with a pH>12. At this stage, the solution is stable for several days at room temperature.

The reaction mixture was diluted with water (200 mL) and extracted with MTBE (3×200 mL). The aqueous solution (2.5/1 DMF/water) was pH adjusted to 8.5 with aqueous HCl (12 N, ca. 10 mL). Assay yield was 95% (based on limiting reagent sodium azide, 27.7 g assay of heterocycle, 0.18 mol). N-methylaniline byproduct and non-reacted N-methylformanilide are extracted in the MTBE layer. The heterocycle remains into the aqueous along with inorganic salts and was >98 A % (at 260 nm).

The product was isolated by first using about 6 eq. of strong acidic ion exchange resin (eq. Dowax or AG-50), then washed with several volume of water then the product was eluted with IPA/water/$NH_3$. The resulting aqueous layer was concentrated to remove water and product was crystallized in IPA. The product 4-N,N-dimethylaminomethyl-5-formyl-1,2,3-triazole was a highly crystalline compound and it has low solibility in dry IPA (4 mg/mL in IPA with KF less than 400 μg/mL). The product can be filtered and dried and it was stable at room temperature under air. 4-N,N-Dimethylaminomethyl-5-formyl-1,2,3-triazole: $C_6H_{10}N_4O$, Mol. wt.: 30 154.17

$^1$H NMR (, 250 MHz, $D_3O$; all peaks are singlets): Free Base: 9.95 ppm (1 H), 4.4 ppm (2 H), 2.80 ppm (6 H). TFA Salt: 10.1 ppm (1 H), 4.5 ppm (6 H), 2.88 ppm (2 H).

Analytical Conditions:

Metachem inertsil ODS-3 (250×4.6); 1.0 mL/min.; detection at 220 and 260 nm; HP 1100; A: $H_2O$ (buffered to pH 7); B: Acetonitrile. —99% A at 0.0 min; 90% A at 10.0 min; 30% A at 20.0 min.

$NaN_3$: 2.85 min (does not abosb @ 260 nm)

4-N,N-dimethylaminomethyl-5-formyl-1,2,3-triazole: 6.75 min

DMP: 7.85 min (does not abosb @ 260 nm)

N-methylformanilide: 19.85 min

N-methylaniline: 22.55 min

EXAMPLE 2

4-N,N-Dimethlaminomethyl-5-formyl-1,2,3-triazole

| Materials | Amount | Mol (equiv) | MW |
|---|---|---|---|
| 1-Dimethylamino-2-propyne | 16.65 g | 0.20 mol | 83.13 |
| EtMgCl (2.0 M in THF) | 110.0 mL | 0.22 mol | |
| N-Methylformanilide | 32.4 g (29.6 mL) | 0.24 mol | 135.17 |
| Sodium azide | 12.35 g | 0.19 mol | 65.01 |
| THF | 90 mL | | |
| DMSO | 400 mL | | |
| Water | 20 mL | | |
| Aqueous 1.0 M HCl | ca. 200 mL | ca. 0.4 mol | |
| Ethyl acetate | 200 mL | | |
| Dowex ® 50 W X8-100 | 590 mL | | |
| Water | 1.8 L | | |
| Acetonitrile/water/triethylamine(6:3:1) | 1.8 L | | |
| Isopropyl alcohol | 1240 mL | | |

1-Dimethylamino-2-propyne (16.65 g, 21.54 mL, 0.2 mol) was dissolved in THE (90 mL) and EtMgCl (2.0 M in TBF, 110.0 mL, 0.22 mol) was added to the resulting yellow homogeneous solution over 10–15 minutes maintaining the temperature at 20–25° C. The reaction mixture was aged at this temperature for 2 hours. The addition was slightly exothermic and was controlled by cooling.

N-Methylformanilide (32.4 g, 29.6 mL, 0.24 mol) was added at room temperature over ca. 10 minutes. The reaction mixture was aged for 60 minutes. The addition was exothermic and was controlled by cooling.

In a separate flask sodium azide (12.35 g, 0.19 mol) was dissolved in DMSO (400 mL) and water (20 mL). The solution was stirred vigorously while the magnesium acetylide mixture was added at 20–25° C. over 15–30 minutes. The reaction was exothermic and was controlled by cooling. The final temperature of the reaction mixture was ~20° C. The solution was yellowish and hazy due to the magnesium salts. The solution was stable for several days at room temperature.

The reaction mixture was pH adjusted with aqueous hydrochloric acid (1.0 M) to pH 7.0–7.5 and diluted with ethyl acetate (200 mL). The layers are separated. The assay yield of 1-dimethylamino-2-propyne was 90% based on the acetylene and 95% based on sodium azide (27.75 g assay of heterocycle, 0.18 mol). About 90% of N-methylaniline byproduct and non-reacted N-methylformanilide are extracted in the ethyl acetate layer.

The aqueous solution was loaded onto the ion exchange resin column (strongly acidic resin Dowexo® 50 W X8-100; 1.7 meq/mL wet, 5 equiv, 1.0 mol, 590 mL) at a flow rate of 4–5 bed volumes per hour. The Dowex® 50 W X8-100 must be properly regenerated prior to use. The resin was then washed with three bed volumes of deionized water (1.8 L) at a flow rate of 4–5 bed volumes per hour to remove the DMSO. The wash solution on the resin was displaced with one bed volume of a mixture of acetonitrile/water/triethylamine (6:3:1). The flow was stopped and the column was aged for 16 hours.

At this stage, the heterocycle was still on the resin. The aging allows equilibration reducing the volume of base wash. The first bed volume was collected and two additional bed volumes are eluted over ca. one hour providing a 95% assay recovery of the heterocycle (26.4 assay g, 0.171 mol). The combined fractions are concentrated to 100 mL. Isopropyl alcohol (600 mL) was added and the mixture was concentrated to 100 mL. This procedure was repeated until the level of water and triethylamine are reduced to <1 V %. The product crystallizes during the solvent switch. The volume was adjusted to ~250 mL. The. triazole aldehyde was filtered, washed with isopropyl alcohol (~40 mL) and dried at 40° C. under vacuum with a nitrogen stream affording 25 g of pure compound (>99 wt %) in an overall 80% isolated yield (based on 1-dimethylamino-2-propyne).

Analytical Conditions:

Metachem inertsil ODS-3 (250×4.6); 0.75 mL/min.; detection at 200, 220 and 240 nm; BP 1100; A: $H_2O$ (buffered to pH 7); B: Acetonitrile. —99% A at 0.0 min; 70% A at 20.0 min; 30% A at 25.0 min; 0% A at 30.0 min.

4-N,N-dimethylaminomethyl-5-formyl-1,2,3-triazole: 2.85 min

N-methylaniline: 4.55 min (strong @ 200 nm; weak @ 220 and 240 nm)

$NaN_3$: 7.5 min (strong @ 200 nm)

Ethyl acetate: 18.60 min

N-methylfonranilide: 25.65 min

EXAMPLE 3

4-N,N-Dimethylaminomethyl-5-formyl-1-1,2,3-triazole

| Materials | Amount | Mol (equiv) | MW |
|---|---|---|---|
| 1-Dimethylamino-2-propyne | 16.65 g | 0.20 mol | 83.13 |
| EtMgCl (2.0 M in THF) | 110.0 mL | 0.22 mol | |
| N-Methylformanilide | 32.4 g (29.6 mL) | 0.24 mol | 135.17 |
| Sodium azide | 12.35 g | 0.19 mol | 65.01 |
| THF | 90 mL | | |
| DMSO | 400 mL | | |
| Water | 20 mL | | |
| Aqueous 1.0 M HCl | ca. 420 mL | ca. 0.42 mol | |
| Ethyl acetate | 200 mL | | |
| Dowex ® 50 W X8-100 | 600 mL | | |
| Water | 1.2 L | | |
| Acetonitrile/water/triethylarmine (6:3:1) | 1.8 L | | |
| 2-Butanol | 640 mL | | |

1-Dimethylamino-2-propyne (16.65 g, 21.54 mL, 0.2 mol) was dissolved in THF (90 mL). EtMgCl (2.0 M, 110.0 mL, 0.22 mol) was added to the yellow homogeneous solution over 10–15 minutes maintaining the temperature at 20–25° C. The reaction mixture was aged for 2 hours. N-Methylformanilide (27.05 g, 24.7 mL, 0.24 mol) was added at room temperature over ca. 10 minutes and the mixture was aged for 60 minutes. The additions of EtMgCl and N-Methylformanilide are slightly exothermic and are controlled by cooling.

The solution of the magnesium acetylide was added to a vigorously stirred solution of sodium azide (12.35 g, 0.19 mol) in DMSO (400 mL) and water (20 mL) at 20–25° C. over 15–30 minutes. The reaction was exothermic and was controlled by cooling. The reaction mixture was yellow and hazy (magnesium salts). The product in the reaction mixture was stable for several days at room temperature.

The reaction mixture was pH adjusted with aqueous HCl (1.0 M) until pH 7.0 to 7.5. The solution was washed with ethyl acetate (200 mL). About 90% of N-methylaniline byproduct and unreacted N-methylformanilide are extracted into the ethyl acetate. The assay yield was 90% based on 1-dimethylamino-2-propyne and 95% based on sodium azide (27.75 g assay of heterocycle, 0.18 mol). No azide was detected by assay (LOD<50 ppm).

The crude reaction mixture was loaded onto the strongly acidic resin Dowex® 50 W X8-100 (1.7 meq/mL wet, 5 equiv, 600 mL) at a flow rate of 4–5 bed volumes per hour.

The Dowex® 50 W X8 must be properly generated prior to use. For fresh resin the bed was washed with 1.5 bed volumes of 90% methanol/water to remove any monomer and other organic soluble impurities. The procedure for 1 L of resin follows: Slurry one liter of Dowex® 50W resin in water, transfer into a suitable column and drain the water to the top of the bed. The bed was washed with 90% methanol/water (1.5 L) at a flow rate of ~25 minutes per bed volume (1 L). One bed volume of water (1 L) was used to rinse the column. A 1 N NaOH solution (3 L) was passed through the column, followed by 1 bed volume of water (1 L) as a rinse. The column was returned to the acid cycle with one bed volume of 1 N HCl (3 L). A final rinse with one bed volume of water and the resin column was ready for use. The column was regenerated as follows: The column was washed with one bed volume of water, and then 3 bed volumes of 1N HCl. A final water wash with one bed volume of water readies the column for reuse. The resin was then washed with 2 bed volumes of deionized water (1.2 L) at a flow rate of 4–5 bed volumes per hour to remove DMSO.

The product was then eluted with a mixture of acetonitrile:water: triethylamine (6:3:1). After 1 bed volume (~600 mL) was added to the column displacing the water wash, the flow was stopped and the column was equilibrated for 1–2 h. Any breakthrough during the solvent switch can be recycled back to the column. At this stage, the product was on the resin. The age allows equilibration reducing the volume of base wash. An additional 1.5 bed volumes (1.2 L) are eluted over ~1 h providing 97% assay recovery of the heterocycle (26.4 assay g, 0.171 mol). The total elution volume was 2.5 bed volumes. Only 1.5 bed volumes are collected leaving one bed volume on the column. A total of 1.5 bed volumes are collected (~900 mL). The rich cuts are concentrated to ~100 mL. 2-Butanol (300 mL) was added and the mixture was concentrated again to 100 mL. 2-Butanol (300 mL) was added and the concentration was repeated until water and triethylamine are reduced to <1% each. During the second concentration, the product crystallized. The final volume was adjusted to 150 mL. The crystalline product was filtered, washed with 2-butanol (~40 mL) and dried at 40° C. under vacuum with a nitrogen stream to afford 25 g of pure triazole aldehyde (>99 wt %) in 80% overall isolated yield based on 1-dimethylamino-2-propyne.

EXAMPLE 4

4-N,N-Dimethylaminomethyl-S-formyl-1,2,3-triazole

| Materials | Amount | Mol (equiv) | MW |
|---|---|---|---|
| 1-Dimethylamino-2-propyne | 457.0 g (593.0 mL) | 5.50 mol | 83.13 |
| EtMgCl (2.0 M in THF) | 3.02 L | 6.05 mol | |
| N-Methylformanilide | 892 g (813 mL) | 6.60 mol | 135.17 |
| Sodium azide | 339.7 g | 5.22 mol | 65.01 |
| THF | 2.5 L + 0.4 L | | |
| DMSO | 11.0 L | | |
| Water | 330.0 mL | | |

A 12-L flask fitted with a mechanical stirrer, thermocouple, nitrogen inlet and 5-L addition funnel was charged with 1-dimethylamino-2-propyne (457 g as is, 593 mL, 5.50 mol) and dry tetrahydrofuran (2.5 L). The resulting yellow homogeneous solution was cooled to ~10° C. and EtMgCl (2.0 M, 3.02 L, 6.05 mol) was added over 30 min while maintaining the temperature at 20–25° C. The reaction mixture was aged at ambient temperature for 2 h. N-Methylformanilide (892 g, 813 mL, 6.60 mol) was then added over 20 min while maintaining the reaction temperature at 20–25° C. The resulting clear yellow-to-green mixture was aged at room temperature for 1 h. The additions of EtMgCl and N-methylformanilide are slightly exothermic. The temperature was controlled by cooling the reaction mixture. During the Grignard addition, ethane was produced (ca. 125 L).

The reaction mixture was transferred into a vigorously stirred DMSO solution (11.0 L) containing sodium azide (339.7 g, 5.22 mol) and water (330 mL, 18.3 mol) over 30 min while maintaining the temperature between 15° C. and 25° C. The 12-L flask was rinsed with THF (0.4 L). The reaction was exothermic and was controlled by cooling the reaction mixture. A 50 L flask was used since the final volume after dilution with toluene and Aliquat® was ~40 L. Assay yield (763 g assay of heterocycle, 4.95 mol) was ~90% based on 1-dimethylamino-2-propyne and ~95% based on sodium azide. The level of residual sodium azide was assayed at <30 ppm. The reaction mixture was yellow-orange and hazy due to magnesium salts. The pH of the mixture was 9.7.

EXAMPLE 4A

4-N,N-Dimethylaminomethyl-5-formyl-1,2,3-triazole: Extractive Isolation Process

| Materials | Amount | Mol (equiv) | Mw |
|---|---|---|---|
| Water | 18 L | | |
| Toluene | 33 L | | |
| Aliquat ® 336 | 6.67 Kg (7.5 L) | 16.50 mol | 404.17 d = 0.884 |
| Glacial acetic acid | 630 mL | 11.0 mol | 60.05 d = 1.049 |
| 2-Butanol | ca. 13 L | | |

To the reaction mixture from Example 4 was added Aliquat® 336 (4.44 kg, 5.0 L, 11.0 mol) and toluene (11.0 L). The mixture was stirred under nitrogen for 30 min and transferred into an extractor. Water (6.0 L) was added affording two phases. The layers are well-mixed and separated. The aqueous layer was back-extracted with a solution of Aliquat® 336 (1.11 kg, 2.75 mol) in toluene (11.0 L). The layers are separated and the aqueous layer was back-extracted once again with Aliquat® 336 (1.11 kg, 2.75 mol) in toluene (11.0 L).

The final aqueous layer was slightly gelatinous due to the suspended magnesium salts. The pH was 9.7. At this stage ~94% of the product (~715 assay g of triazole aldehyde, 4.65 mol) has been extracted into the combined organic layers.

The combined organic layers also contain ~35 A % of DMSO, as compared to the triazole aldehyde, Aliquat® 336, the N-methylaniline byproduct and excess of N-methylforrnanilide.

The combined organic layers are washed with water (6.0 L) to remove the DMSO. Less than 1% of triazole aldehyde was extracted into the aqueous layer (ca. 0.6%). The organic layer contains ca. 3 A % of DMSO. The resulting combined organic layer was washed with water (4.5 L) containing glacial acetic acid (630 mL, 11.0 mol) to release the triazole aldehyde. The layers are separated and the organic layer was washed once again with water (2.0 L).

The two extractions recover 95% of the triazole aldehyde (85% in first one and 10% in second one). The N-methylaniline byproduct and the excess N-methylformanilide remain in the organic layer. At this stage an 86% overall recovery (~660 assay g, 4.25 mol) of the triazole aldehyde has been achieved.

The combined aqueous layers are concentrated to 1.5 L. 2-Butanol (12 L) was added and the mixture was concentrated to ~2 L. This procedure was repeated until the level of water was reduced to <0.5 V %. The product crystallizes during the solvent switch.

The volume was adjusted to ~3 L. The triazole aldehyde was filtered, washed with 2-butanol (1.0 L) and dried at 40° C. under vacuum for 16 h with a nitrogen stream affording 562 g of pure triazole aldehyde (>99.5 A %, >98.5 wt %) as an off-white shiny crystalline solid. The overall isolated yield was 66% based on 1-dimethylamino-2-propyne. The loss to the mother liquors (98 assay g) was 15%.

EXAMPLE 4B

4-N,N-Dimethylaminomethyl-5-formyl-1,2,3-triazole: Salt Filtration Isolation Process

| Materials | Amount | Mol (equiv) | MW |
|---|---|---|---|
| Water | 18.5 L | | |
| Toluene | 14.5 L | | |
| Aliquat ® 336 | 6.67 kg (7.5 L) | 16.50 mol | 404.17 d = 0.884 |
| Solka-floc | 3000 mL | | |
| Glacial acetic acid | 630 mL | 11.0 mol | 60.05 d = 1.049 |
| 2-Butanol | ca. 13 L | | |

The same mixture of the sodium salt of the triazole aldehyde in DMSO/THF from Example 4 was alternatively treated as follows: To the reaction mixture was added Aliquat® 336 (6.67 kg, 7.5 L, 16.5 mol) and toluene (11.0 L). The mixture was yellow-orange in color and hazy due to magnesium salts. This mixture was aged under nitrogen for 2 h. The salts are removed by filtration through a pad of solka-floc (3000 mL; ~3 inches in a 6-L sintered-glass funnel). The filtration removes the sodium chloride formed by the displacement of the Aliquot chloride with the sodium salt of the triazole. This leaves the Aliquot as a soluble salt of the triazole in toluene. Filtration of the mixture takes ~1.5 h. About 1.5 inches of salts relative to the 3 inches of the solka-floc cake are removed.

The pad of solka-floc was rinsed with toluene (3.5 L). The resulting hazy-yellow filtrate was transferred into an extractor and diluted with water (6.0 L). The mixture separates into two phases. The layers are well-mixed and separated. The resulting aqueous layer was slightly gelatinous due to the magnesium salts. The pH was 9.7. At this stage ~89% of product (~680 assay g, 4.40 mol) has been extracted. The toluene layer contains the triazole aldehyde along with ~35 A % of DMSO (relative to the triazole aldehyde), Aliquat® 336, the N-methylaniline byproduct and excess N-methylformanilide.

The organic layer was washed with water (6.0 L) to remove the DMSO. The toluene layer contains ~3 A % of DMSO. Less than 1% of the triazole aldehyde was lost in the aqueous layer (~0.6%). The organic layer was washed with water (4.5 L) containing glacial acetic acid (630 mL, 11.0 mol) to release the triazole aldehyde. The layers are separated and the organic layer was washed with water (2.0 L). These two extractions recover 94% of the triazole aldehyde (85% in the first and 9% in the second). The N-methylaniline byproduct and excess N-methylformanilide remain in the organic layer. At this stage 81% overall of triazole aldehyde (~620 assay g, 4.0 mol) has been recovered. The combined aqueous layers are concentrated to ~1.5 L. 2-Butanol (12 L) was added and the mixture was concentrated to ~2 L. This procedure was repeated until the level of water was reduced to <0.5 V %. The product crystallizes during the solvent switch.

The volume was adjusted to ~3 L. The solid was filtered, washed with 2-butanol (1.0 L) and dried at 40° C. under vacuum with a nitrogen stream for 16 h to afford 520 g of pure triazole aldehyde (>99.5 A %, >98.5 wt %) as an off-white shiny crystalline solid. The overall isolated yield was 61% (based on 1-dimethylamino-2-propyne). The loss to the mother liquors (95 assay g) was 16%.

EXAMPLE 5

4-N,N-Dimethylaminomethyl-5-formyl-1,2,3-triazole

| Materials | Amount | Mol (equiv) | MW |
|---|---|---|---|
| 1-Dimethylamino-2-propyne | 26.2 g | 0.315 mol | 83.13 |
| EtMgCl (2.0 M in THF) | 173 mL | 0.346 mol | |
| N-Methylformanilide | 51.1 g (46.7 mL) | 0.378 mol | 135.17 |
| Sodium azide | 19.5 g | 0.300 mol | 65.01 |
| THF | 70 mL | | |
| DMSO | 500 mL + 90 mL + 60 mL | | |
| Water | 8.1 mL | 0.450 mol | 18.0 |
| Hydrogen chloride HCl (4.2 N/IPA) | 145 mL | 0.610 mol | |
| Piperidine | 29.4 g (34.2 mL) | 0.346 mol | 85.15 |
| Ethyl acetate | 310 mL + 150 mL | | |
| Trifluoroacetic acid (TFA) | 26.7 g (18.0 mL) | ca. 0.234 mol | 114.02 (d: 1.48) |
| Solka-floc | ca. 100 mL | | |
| 2-Propanol (IPA) | 360 mL + 40 mL | | |

A 500 mL flask fitted with an over-head stirrer, a thermocouple, an inlet of nitrogen and a 250 mL dropping funnel was charged with 1-dimethylamino-2-propyne (26.2 g not corrected for purity, 0.315 mol) and TBF (70 mL). The resulting yellow homogeneous solution was cooled over an ice bath to ca. +10° C. and EtMgCl (2.0 M, 173 mL, 0.346 mol) was added over 30 minutes maintaining the temperature between +20 and +25° C. After completion of the addition, the reaction mixture was warmed to room temperature (20 to 25° C.) and aged for 2 hours. N-Methylformanilide (51.1 g, 46.7 mL, 0.378 mol) was then added over ca. 20 minutes while maintaining the reaction temperature between +20 and +25° C. The resulting yellow-green (clear homogeneous) mixture was aged at room temperature for 1 hour. The additions of EtMgCl and N-methylformanilide are slightly exothermic. During the Grignard addition, ethane was produced (ca. 7 L).

The reaction mixture was added into a vigorously stirred solution of DMSO (500 mL) containing sodium azide (19.5 g, 0.3 mol) and water (8.1 mL, 0.45 mol) over 30 minutes while maintaining the temperature between +15° C. and +25° C. The reaction was exothermic and was controlled by cooling the reaction mixture. The final temperature of the batch was ca. +20° C. The assay yield was 91% based on 1-dimethylamino-2-propyne and 96% based on sodium azide (44.2 g assay of heterocycle, 0.287 mol). The level of remaining sodium azide was assayed at <30 ppm. The reaction mixture was yellow-orange and hazy and the pH was 9.7.

Hydrogen chloride (4.2 N HCl in IPA, 145 mL, 0.61 mol) was added over ca. 15 minutes while maintaining the temperature between +20 and +25° C. After completion of the addition, the resulting yellow-orange slurry of magnesium salts was concentrated to remove THF and IPA. The mixture was filtered through a pad of solka-floc (100 mL; ca. 0.5 inch in a 600 mL sintered glass funnel) to remove the insoluble salts. The pad of solka-floc was rinsed with DMSO (90 mL). The resulting filtrate was clear yellow-orange. The pH was 8.25. The target for the pH was 7.0 to 8.5, measured from an aliquot of the solution diluted with an equal volume of water. Using TFA instead of HCl (4N in IPA) for the neutralization led to a lower recovery of dimer (ca. 70% vs 85%) which was likely due to a poorer removal of inorganic salts.

Piperidine (34.2 mL, 0.346 mol) in ethyl acetate (310 mL) (344 mL, ~1 M) was added to the resulting DMSO filtrate over 2–3 hours and the reaction was aged at room temperature for ca. 16 h. The dimer adduct crystallizes during the addition of piperidine to give a stirrable slurry.

The resulting yellow slurry was filtered to afford the dimer adduct as a white solid, which was washed with DMSO (60 mL) and ethyl acetate (150 mL), and dried at 40° C. under vacuum with a nitrogen stream for 16 hours to afford 62.1 g of product (95 A %, ca. 87 wt %) as a white solid. The isolated yield was 74.5% based on 1-dimethylamino-2-propyne and 78% based on sodium azide (54.0 g assay of dimer, 0.117 mol). The filtration was fast. The solubility of the product in the filtrate was ca.10 g(L as triazole-aldehyde equivalent, which represents a yield loss of 18%. The pH of filtrate was 10.3. The dimer was pure. The low wt % (87 wt %) was due to residual DMSO, which does not affect the next step.

The piperidine adduct (62.1 g, 87 wt %, 54.0 g assay, 0.117 mol) was slurried in IPA/water (98:2, 365 mL). TFA (26.7 g, 18.0 mL, 0.234 mol) was added over 10 minutes maintaining the temperature at 20–25° C. The triazole aldehyde was liberated during the pH adjustment. The product crystallized from the reaction mixture.

The slurry was stirred for 2 hours at room temperature. The triazole-aldehyde was filtered, washed with IPA (40 mL) and dried at 40° C. under vacuum with a nitrogen stream for 16 hours to afford 30.5 g of pure product (>99.9 A %, >99.5 wt %) as a white crystalline solid. The isolated yield was 63% based on 1-dimethyl-amino-2-propyne and 65.5% based on sodium azide.

EXAMPLE 6

4-Benzyl-2-hydroxy-1,4-oxazin-3-one

| Materials | MW | Density | Amount | mol | Equiv. |
|---|---|---|---|---|---|
| N-Benzylethanolamine (96%) | 151.21 | 1.065 | 7.80 kg | 49.5 (assay) | 1.0 |
| Glyoxylic acid (50% in water) | 74.04 | 1.342 | 12.60 L | 114.2 | 2.31 |
| Tetrahydrofuran | 72.11 | 0.889 | 27.0 L | — | — |
| 4-Benzyl-2-hydroxy-1,4-oxazin-3-one seed | 207.23 | — | 0.252 kg | 1.24 | 0.025 |
| Water | 18.0 | 1.00 | 63.0 L | — | — |

A solution of THF (27.0 L) and 50% aqueous glyoxylic acid (12.6 L; 16.9 kg) was heated to reflux and N-benzylethanolamine (7.8 kg) was added over 45 min. The resulting mixture was refluxed for 21 h. Then the THF was distilled under atmospheric pressure while maintaining a constant volume by simultaneous addition of water (27 L). Upon completion of the distillation (<8 vol % of THF in batch) the ixture was cooled from approximately 95–100 to 79–81° C. and was optionally seeded with 4-benzyl-2-hydroxy-1,4-oxazin-3-one (250 g). Upon further cooling to room temperature the product crystallized. Crystalline 4-benzyl-2-hydroxy-1,4-oxazin-3-one was filtered, washed with water and then dried in a vacuum oven at about 60° C. under a stream of $N_2$ (72–76% yield); m.p. 134° C.

EXAMPLE 7

3,5-Bis(trifluoromethyl)bromobenzene

| Materials | MW | Density | Amount | Mmol | Equiv. |
|---|---|---|---|---|---|
| 1,3-Bis(trifluoro-methyl)benzene | 214.1 | 1.38 | 107 g | 500 | 1.0 |
| 96% $H_2SO_4$ | | | 142 mL | | |
| Glacial HOAc | | | 22 mL | | |
| 1,3-Dibromo-5,5-dimethylhydantoin | 285.93 | | 77.25 g | 270 | 1.08 ($Br^+$) |
| 5 N Aq NaOH | | | 75 mL | | |

A vigorously stirred solution of 1,3-bis(trifluoromethyl) benzene (107 g) in a mixture of glacial acetic acid (22 mL) and concentrated sulfuric acid (142 mL) was added 1,3-dibromo-5,5-dimethylhydantoin (77.25 g) at 25° C. The exothermic reaction raised the temperature to approximately 40° C. After aging at 45° C. for 4.5 h, the mixture was cooled to approximately 0° C. and poured into cold water (250 mL). After washing with 5N NaOH (75 mL) the organic layer contained 137 g of the desired 3,5-bis(trifluoromethyl)-1-bromobenzene by assay (94% yield). This product was used in the next step without further purification.

EXAMPLE 8

1-(3,5-Bis(trifluoromethyl)phenyl)ethan-1-one

| Materials | MW | Density | Amount | Mmol | Equiv |
|---|---|---|---|---|---|
| 3,5-Bis(trifluoro-methyl)-bromobenzene | 293.03 | 1.699 g/L | 29.3 g | 98.0 | 1.0 |
| Magnesium granules, 20 mesh | 24.3 | | 5.10 g | | 2.1 |
| Acetic Anhydride | 102.1 | 1.08 g/L | 40 mL | 423 | 4.5 |
| THF (KF = 60 μg/mL) | | | 260 mL | | |
| MTBE | | | 650 mL | | |
| Water | | | 300 mL | | |
| 50% NaOH | | | 40 mL | | |

A solution of 3,5-Bis(trifluoromethyl)bromobenzene (29.3 g) in 30 mL of THF was added to a mixture of magnesium granules (5.10 g) in THF (200 mL) heated at reflux (the reaction was initiated with approximately 5 mL of the bromide solution; the remainder was added slowly over 1 h). The mixture was aged for 30 min at reflux, cooled to RT and added over 1 h to a solution of acetic anhydride (40 mL) in THF (40 mL) maintained at −15° C. The resulting dark brown mixture was warmed to 10° C. in a water bath, and water (300 mL) was added. The pH of the vigorously stirred biphasic mixture was adjusted to 8.0 using 50% NaOH. MTBE (300 mL) was added, the layers were separated and the aqueous layer was further extracted with MTBE (3×150 mL). The organic layers were combined and concentrated in vacuo (bath at 30–35° C.; 50–80 torr). The concentrate was then distilled at atmospheric pressure to provide the pure product (20.7 g; 82% yield) with a boiling point of 187–189° C.

EXAMPLE 9

(R)-1-(3,5-bis(Trifluoromethyl)phenyl)ethan-1-ol

| Materials | MW | Mol | Amt |
|---|---|---|---|
| 1-(3,5-Bis(trifluoromethyl)-phenyl)ethan-1-one | 256.15 | 11.7 | 3 Kg |
| $[RuCl_2(p-cymene)]_2$ (Cym = p-cymene (4-isopropyltoluene)) | 612.40 | 0.03 | 18.4 g |
| (S,R)-cis-Aminoindanol | 149.20 | 0.06 | 9.0 g |
| NaOH | 5 N ($H_2O$) | 0.14 | 28 mL |
| IPA | | | 21 L |
| HCl | 1 N ($H_2O$) | | 21 L |
| Heptane | | | 21 L |
| 1,4-Diazabicyclo[2.2.2]octane | 112.18 | ~6.6 | ~740 g |

(DABCO)

A solution of $[RuCl_2(p-cymene)]_2$ (18.4 g), (1S,2R)-cis-1-amino-2-indanol (9.0 g) and 1-(3,5-bis(trifluoromethyl) phenyl)ethan-1-one (3 kg) in 2-propanol (21 L) was stirred for 30 min and thoroughly degassed under vacuum. Then M sodium hydroxide (28 mL) was added and the mixture was aged for 4–6 h to achieve complete conversion of the starting material. The reaction mixture was poured into 1 N HCl (21 L) and extracted with heptane (2×10.5 L). The combined organic layers were washed with brine and 1,4-diazabicyclo [2.2.2]octane (740 g) was added. The solution was concentrated to approximately 4 mL/g of alcohol (KF<200 μg/mL; 2-propanol<5 vol %). The mixture was seeded at 40° C., allowed to cool to RT to from a seedbed and then cooled to 0° C. The crystalline product was filtered, washed with cold heptane and dried to provide the DABCO complex (75–80% yield; e.e.>99%).

EXAMPLE 10

(2R, 2-Alpha-R)-4-benzyl-2-[1-[3,5-bis (trifluoromethyl)phenyl]ethoxy-1,4-oxazin-3-one (Process 1)

| Materials | Kg | L | mol | MW | density | mol % |
|---|---|---|---|---|---|---|
| 4-Benzyl-2-hydroxy-1,4-oxazin-3-one | 2.14 | | 10.3 | 207.2 | | 100 |
| Trifluoroacetic anhydride | 2.16 | 1.46 | 10.3 | 210.0 | 1.487 | 100 |
| (R)-(3,5-bis(trifluoro-methyl)phenyl)ethan-2-ol (49.5 wt % solution in acetonitrile) | 5.11 | 5.13 | 9.80 | 258.2 | 0.996 | 95 |
| Boron trifluoride etherate | 0.73 | 0.65 | 5.14 | 141.9 | 1.120 | 50 |
| 5 N NaOH(aq) | 7.60 | 38.0 | | | 370 | |
| 3,7-Dimethyloctan-3-ol | 4.90 | 5.93 | 31.0 | 158.3 | 0.826 | 300 |
| Potassium t-butoxide (solid) | 0.75 | | | 112.2 | | 65 |
| Acetic acid (neat) | 0.62 | 0.59 | 10.3 | 60.05 | 1.049 | 100 |
| Acetonitrile | | 5.3 | | | | |
| Heptane | | 27 | | | | |
| 5% Sodium bicarbonate (aq) | | 5 | | | | |
| Water | | 23 | | | | |

Trifluoroacetic anhydride (2.16 kg) was added over 10 min to a dry (KF<100 μg/mL) slurry of lactam lactol (2.14 kg) in acetonitrile (5 L) cooled at 5° C. The temperature rose from 5 to 30° C. and the solids dissolved. The solution was aged for 1 h between 17–25° C. before a concentrated solution of (R)-(3,5-bis(trifluoromethyl)phenyl)ethan-2-ol in acetonitrile (5.11 kg of solution containing 2.53 kg of alcohol) was added followed by BF₃ etherate (0.65 L). The temperature rose from 17 to 27° C. and the mixture was aged for 4 h before 5 M NaOH (7.6 L) was added slowly while maintaining the temperature below 27° C. followed by 3,7-dimethyloctan-3-ol (5.9 L). The resulting mixture was distilled at atmospheric pressure until the vapor temperature reached 92° C. and most of the acetonitrile was distilled off. Water (5 L) and heptane (8 L) were added and the mixture was warmed to 45° C. The organic layer was separated, washed with water (13 L) at 45–50° C. and then diluted with heptane (16 L). The solution was dried via an azeotropic distillation until KF<130 μg/mL (6 L of distillate collected; 3 L of fresh heptane added). The solution was cooled to RT and seeded with the (R,R) diastereomer (50 mg). Upon formation of a seedbed the slurry was cooled to −10° C. and potassium tert-butoxide (752 g) was added in one portion. The mixture was aged between −12 and −7° C. for 8.5 h when virtually all of the undesired diastereomer had been converted to the desired (R,R) diastereomer according to HPLC analysis. Acetic acid (0.59 L) was added followed by a 5% NaHCO₃ in water solution (5 L). The biphasic mixture was warmed to 45–50° C. The organic layer was separated, washed with water (5 L) at 45-50° C. and concentrated via distillation at atmospheric pressure to a total volume of 24 L (12 L of distillate collected). Upon cooling to 35° C. a seedbed formed. The slurry was cooled to −10° C. and then filtered. The solids were washed with cold heptane (4.5 L) and dried in vacuo to provide the pure product (3.66 kg; 83% overall yield).

EXAMPLE 11

(2R, 2-Alpha-R)-4-benzyl-2-[1-[3,5-bis(trifluoromethyl)phenyl]ethoxy-1,4-oxazin-3-one (Process 2)

| Materials | Kg | L | mol | MW | density | mol % |
|---|---|---|---|---|---|---|
| 4-Benzyl-2-hydroxy-1,4-oxazin-3-one | 2.03 | | 9.80 | 207.2 | | 100 |
| Trifluoroacetic anhydride | 2.06 | 1.38 | 10.3 | 210.0 | 1.487 | 100 |
| (R)-(3,5-bis(trifluoromethyl)phenyl)ethan-2-ol (49.5 wt % solution in acetonitrile) | 4.85 | 4.87 | 9.30 | 258.2 | 0.996 | 95 |
| Boron trifluoride etherate | 0.69 | 0.62 | 4.86 | 141.9 | 1.120 | 50 |
| 5 N NaOH(aq) | | 8.1 | 40.5 | | | 410 |
| 3,7-Dimethyloctan-3-ol | | 1.68 | 2.03 | 10.6 | 158.3 | 0.826 |
| Potassium 3,7-dimethyloct-3-oxide (48.7 wt % in heptane, 1.99 M) | 1.09 | 1.36 | 2.70 | 196.4 | 0.803 | 28 |
| Acetic acid (neat) | 0.28 | 0.29 | 4.66 | 60.05 | 1.049 | 47 |
| Acetonitrile | | 4.8 | | | | |
| Heptane | | 21 | | | | |
| 5% Sodium bicarbonate (aq) | | 4.1 | | | | |
| Water | | 20.4 | | | | |

Trifluoroacetic anhydride (2.056 kg) was added over 10 min to a dry (KF<140 μg/mL) slurry of lactam lactol (2.03 kg) in acetonitrile (4.8 L) cooled at 5° C. The temperature rose from 5 to 34° C. and the solids dissolved. The solution was aged for 1 h between 17–25° C. before a concentrated solution of (R)-(3,5-bis(trifluoromethyl)phenyl)ethan-2-ol in acetonitrile (4.85 kg of solution containing 2.40 kg of alcohol) was added followed by BF₃ etherate (0.62 L). The temperature rose from 17 to 28° C. and the mixture was aged for 2 h before 5 M NaOH (8.1 L) was added slowly while maintaining the temperature below 27° C., followed by 3,7-dimethyloctan-3-ol (2.0 L). The resulting mixture was distilled at atmospheric pressure until the vapor temperature reached 92° C. and most of the acetonitrile was distilled off (8.1 L of distillate collected). Water (4.1 L) and heptane (12.2 L) were added and the mixture was warmed to 45° C. The organic layer was separated, washed with water (12.2 L) at 45–50° C. and then diluted with heptane (6 L). The solution was dried via an azeotropic distillation until KF<130 μg/mL (7.8 L of distillate collected). The solution was cooled to RT and seeded with the (R,R) diastereomer (50 mg). Upon formation of a seedbed the slurry was cooled to −11° C and potassium 3,7-dimethyloct-3-oxide (1.09 kg; 48.7 wt % solution in heptane) was over 10 min. The mixture was aged between −12 and −7° C. for 5 h during which virtually all of the undesired diastereomer had been converted to the desired (R,R) diastereomer according to HPLC analysis. Acetic acid (0.28 L) was added followed by a 5% NaHCO₃ in water solution (4.1 L). The biphasic mixture was warmed to 45–50° C. The organic layer was separated, washed with water (4.1 L) at 45–50° C. and concentrated via distillation at atmospheric pressure to a total volume of 16 L (4.1 L of distillate collected). The solution was seeded at 45° C. and then allowed to cool to RT. The slurry was cooled to 5° C., aged for 1.5 h and then filtered. The solids were washed with cold heptane (3.0 L) and dried in vacuo to provide the title product (3.51 kg; 84% overall yield).

EXAMPLE 12

2-(R)-(1-(R)-(3,5-bis(Trifluoromethyl)phenyl)-ethoxy)-3-(S)-(4-fluorophenyl)-morpholine A solution of 4-fluorophenylmagnesium bromide in TBE (150 mL; 0.93 M) was slowly added to a solution of (2R, 2-alpha-R)-4-benzyl-2-[1-[3,5-bis(trifluoromethyl)phenyl]ethoxy-1,4-oxazin-3-one (49.5 g) in THF (50 mL) between 20 and 25° C. The resulting clear solution was aged for 30 min and then added slowly into cold methanol (100 mL) such that T<20° C. A solution of 4-toluenesulfonic acid monohydrate (42.1 g) in methanol (50 mL) was added to the slurry followed by the 5% Pd/C catalyst (16.5 g; 55 wt % wet). The resulting mixture was hydrogenated under 5 psi of hydrogen at RT for 3 h. The catalyst was filtered and washed with methanol (100 mL). The combined filtrates were concentrated via distillation at atmospheric pressure to a total volume of approximately 350 mL. The distillation was continued while keeping the volume constant at 350 mL via slow addition of 4-methyl-2-pentanone (methyl-isobutyl ketone; MIBK; 450 mL). Upon completion of the distillation, the resulting slurry was allowed to cool to 20–30° C. and washed with 500 mL of a solution of trisodium citrate dihydrate (10 wt %) and sodium bicarbonate (1.0 M) in water. Toluene sulfonic acid (1 eq) is added to the organic layer and the clear solution is concentrated under atmospheric pressure to a total volume of approximately 180 mL. The resulting product slurry is cooled from 118° C. to 5° C. and filtered. The solids are washed with methyl-isobutyl ketone (MIBK) and dried in vacuo at 40° C. to afford 2-(R)-(1-(R)-(3,5-bis(trifluoromethyl)phenyl)-ethoxy)-3-(S)-(4-fluorophenyl)morpholine TsOH salt.

EXAMPLE 13

2-(R)-(1-(R)-(3,5-bis(Trifluoromethyl)phenyl)-ethoxy)-4-(5-(dimethylamino)-methyl-1,2,3-triazol-4-yl)methyl-3-(S)-(4-fluorophenyl)morpholine 2-(R)-(1-(R)-(3,5-bis(trifluoromethyl)phenyl)-ethoxy)-3-(S)-(4-fluorophenyl)morpholine TsOH salt (609g, 1 mol)

and 4-N,N-dimethylaminomethyl-5-formyl-1,2,3-triazole (225 g, 1.5 mol) are suspended in 3 L of toluene and 1 L of DMF. The resulting suspension was stirred for 30 minutes, then 1 eq. of sodium triacetoxyborohydride (212 g, 1 mol) was added. After 30 minutes, another portion of sodium triacetoxyborohydride (212g, 1 mol) was added. The resulting solution/suspension was aged at 25° C. for 5 hours and the reaction was completed when starting material secondary amine was less than 0.1A % (at 220 nm) as judged by LC. When the reaction was completed, 2 eq. of 1N HCl (2 L, 2 mol) was added and the reaction mixture was aged for 4 hours (to break some boron complexes). The solution was then neutralized back to pH=8~9 with NaOH or $Na_3PO_4$ and extracted with toluene (3 L) and organic layer was washed twice with water and concentrated to obtain 2-(R)-(1-(R)-(3,5-bis(trifluoro-methyl)phenyl)-ethoxy)-4-(5-(dimethylamino)-methyl-1,2,3-triazol-4-yl)methyl-3-(S)-(4-fluorophenyl)morpholine.

EXAMPLE 14

2-(R)-(1-(R)-(3,5-bis(Trifluoromethyl)phenyl)-ethoxy)-4-(5-(dimethylamino)-methyl-1,2,3-triazol-4-yl)methyl-3-(S)-(4-fluorophenyl)moroholine

| Materials | Amount | MW |
|---|---|---|
| 2-(R)-(1-(R)-(3,5-bis(trifluoromethyl)-phenyl)ethoxy)-3-(S)-(4-fluorophenyl)-morpholine TsOH salt | 609 g (1 mol) | 609 |
| 4-N,N-dimethylaminomethyl-5-formyl-1,2,3-triazole | 200 g (1.3 mol) | 154.17 |
| NaBH(OAc)$_3$ | 414 g (95 wt %, 1.9 mol) | 211.94 |
| DMAC (Dimethylacetamide) | 2.7 L | |

To 4-N,N-dimethylaminomethyl-5-formyl-1,2,3-triazole (200 g, 1.3 mol) in dimethylacetamide (1.7 L) at 0~–5° C. was charged with 2-(R)-(1-(R)-(3,5-bis(trifluoromethyl) phenyl)ethoxy)-3-(S)-(4-fluorophenyl)morpholine TsOH salt (609 g, 1 mol). The resulting slurry was transferred into another vessel and 0.3 L of dimethylacetamide was used for the rinse. Then a solution of NaBH(OAc)$_3$ (414 g, 1.9 mol) in dimethylacetamide (0.7 L) was added (prepared off line using another vessel). It was necessary to cool down the solution to 0~–5° C. to avoid side reaction during charging with the secondary amine. The reaction was slow at 0 to –5° C. and it was slightly exothermic. The reaction solution was slowly heated up to 40° C. and was maintained for 1 hour to complete the reaction. The reaction was judged completely by HPLC when the secondary amine was less than 0.1A % (220nm).

Aqueous HCl (1.33 L, 3 N, 4 mol) was then added (maintaining 40° C. with cooling during HCl charge) and aged for 2 hours at 40° C. (to destroy some excess sodium triacetoxyborohydride and to break some boron complexes). Toluene (3 L) was added, then the solution was neutralized back to pH=8–9 with NaOH (5 N, ~2 L). It was necessary to add toluene (3 L) before adjusting pH to avoid free base of the product precipitate as a gum ball. Additional water (2.1 L) was added and the organic layer was separated, washed twice with water (4 L) and constant volume distillation to remove the water azeotropically to give a solution of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine.

EXAMPLE 15

2-(R)-(1-(R)-(3,5-bis(Trifluoromethyl)phenyl)-ethoxy)-4-(5-(dimethylamino)-methyl-1,2,3-triazol-4-yl)methyl-3-(S)-(4-fluorophenyl)morpholine Hydrochloride A crude solution of 2-(R)-(1-(R)-(3,5-bis(trifluoromethyl) phenyl)-ethoxy)-4-(5-(dimethylamino)methyl-1,2,3-triazol-4-yl)methyl-3-(S)-(4-fluorophenyl)morpholine (1.64 kg, 2.85 mol) solvent switch to ethyl acetate (~8 L, KF<200 µg/mL), and was titrated with HCl in IPA (4.0 M). The end point was monitored by taking 1 mL solution, diluting with 2 mL IPA and 2 mL of water and checking its pH, to a preferred end point of 4.6~4.8. After reaching its end point, the amount of IPA was adjusted to 0.5 mL/g of 2-(R)-(1-(R)-(3,5-bis(trifluoromethyl)-phenyl)ethoxy)4-(5-(dimethylamino)methyl-1,2,3-triazol-4-yl)methyl-3-(S)-(4-fluorophenyl)morpholine HCl salt (0.87 L total including IPA from HCl source). Gas chromatography was used to determine the amount of ethyl acetate and it was adjusted to 5 mL/g of 2-(R)-(1-(R)-(3,5-bis(trifluoromethyl)phenyl) ethoxy)4-(5-(dimethyl-amino)methyl-1,2,3-triazol-4-yl) methyl-3-(S)-(4-fluorophenyl)morpholine HCl. Heptane was then added, where a first portion (4.4 L) was added at once, then the solution was seeded with Form I and aged for two hours, then the remaining heptane (24.4 L) was added over a period of 6 hours and aged for 2 hours before filtering. The resulting cake was washed with ethyl acetate/heptane (5 L, 1/2 mixture) and then dried in oven at 40° C. with nitrogen. The water amount was controled wherein Karl Fisher titration of the whole solution did not exceed 400 µg/mL.

EXAMPLE 16

2-(R)-(1-(R)-(3,5-bis(Trifluoromethyl)phenyl)-ethoxy)-4-(5-(dimethylamino)-methyl-10 1,2,3-triazol-4-yl)methyl-3-(S)-(4-fluorophenyl) moroholine Hydrochloride To a solution of 2-(R)-(1-(R)-(3,5-bis(trifluoromethyl) phenyl)-ethoxy)-4-(5-(dimethylamino)methyl-1,2,3-triazol-4-yl)methyl-3-(S)-(4-fluorophenyl)-morpholine (1.417 kg, 2.46 mol) in ethyl acetate (7.5 L) at room temperature is added a solution of HCl in isopropanol (approx. 495 mL). The end point was monitored by taking 1 mL solution, diluting with 2 mL IPA and 2 mL of water and checking its pH, to a preferred end point of 4.6~4.8. After reaching its end point, an additional amount of isopropanol (255 mL) was added to bring the total volume of isopropanol to 750 mL. Heptane (4 L) was added followed by seed of Form I. The mixture was aged for two hours, then additional heptane (20.75 L) was added over a period of 6 hours and the mixture was aged for 16 hours before filtering. The resulting solid was collected by filtration and the cake was washed with ethyl acetatelheptane (5 L, 1/2 mixture) and then dried to afford 1.32 kg of 2-(R)-(1-(R)-(3,5-bis(trifluoromethyl) phenyl)-ethoxy)4-(5-(dimethylamino)methyl-1,2,3-triazol-4-yl)methyl-3-(S)-(4-fluoro-phenyl)morpholine hydrochloride.

EXAMPLE 17

2-(R)-(1-(R)-(3,5-bis(Trifuoromethyl)phenyl)-ethoxy)-4-(5-(dimethylamino)-methyl-1,2,3-triazol-4-yl)methyl-3-(S)-(4-fluorophenyl)morpholine Hydrochloride Based on the amount of 2-(R)-(1-(R)-(3,5-bis (trifluoromethyl)phenyt)-ethoxy)4-(5-(dimethylamino)

methyl-1,2,3-triazol-4-yl)methyl-3-(S)-(4-fluoro-phenyl) morpholine free base (0.546 kg, 0.95 mol) and titration of HCl, a first portion of anhydrous HCl in IPA (214 mL, 0.9 eq., 4 M HCl in IPA concentration) was added into a solution of free base 2-(R)-(1-(R)-(3,5-bis(trifluoromethyl)phenyl)-ethoxy)-4-(5-(dimethylamino)methyl-1,2,3-triazol-4-yl) methyl-3-(S)-(4-fluorophenyl)-morpholine in toluene at 20–25° C. The pH was measured, then several smaller portions of HCl (12 mL, 0.05 eq.) were added the end point of a target pH was 4.6–4.8 was reached. The pH was measured with a pH meter by making a homogeneous solution which contains 1 mL of reaction mixture, 3 mL of IPA and 2 mL of water. n-Heptane (0.5 L) was added at once, followed with 2-(R)-(1-(R)-(3,5-bis(trifluoro-methyl)-phenyl)ethoxy)-4-(5-(dimethylamino)methyl-1,2,3-triazol-4-yl)methyl-3-(S)-(4-fluorophenyl)morpholine HCl seed (5.5g, ~1%). The solution was aged for 1 hour, then the remaining n-heptane (7.7 L) was added over a period of 4~6 hours and the slurry was aged for 2 hours. The solid was filtered and washed once with toluene/n-heptane mixture (4.35 L, 1:3). The product was dried under vacuum with nitrogen at 40° C. for I day (550g, 0.9 mol, 90% overall).

The resulting crude 2-(R)-(1-(R)-(3,5-bis (trifluoromethyl)phenyl)-ethoxy)-4-(5-(dimethylamino) methyl-1,2,3-triazol-4-yl)methyl-3-(S)-(4-fluoro-phenyl) morpholine HCl salt (0.55 kg) was dissolved in 3 L of ethyl acetate and 0.3 L of isopropanol with a Karl-Fisher titration of between 2000±100 µg/mL at ~25° C., then inline filtered into a clean vessel. A first portion of n-heptane was added at once (0.825 L), then seeded with Form I crystal of 2-(R)-(1-(R)-(3,5-bis(trifluoromethyl)-phenyl)ethoxy)-4-(5-(dimethylamino)methyl-1,2,3-triazol-4-yl)methyl-3-(S)-(4-fluorophenyl)morpholine (27.5 g, 5%), and aged for 1 hour. A second portion of n-heptane (1.375 L) was added over 4 hours, aged for 1 hour and a third portion of n-heptane (5.5 L) was added over 4 hour. After the addition, aged for 1 hour, then filtered and cake will be washed with 25% ethyl acetate/n-heptane (1 L). The final product was dried under vacuum with nitrogen sweeping at 40° C. until an acceptable level of solvent was reached.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compound of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A polymorphic form of the compound 2-(R)-(1-(R)-(3, 5-bis(trifluoromethyl)phenyl)ethoxy)-4-(5-(dimethylamino) methyl-1,2,3-triazol-4-yl)methyl-3-(S)-(4-fluorophenyl) morpholine hydrochloride characterized by an X-ray powder diffraction pattern with key reflections at approximately: 7.0, 10.6, 13.1, 14.1, 16.4, 17.9, 20.4, 21.3, 22.0, 23.8, 24.8, 25.6, and 26.9° (2 theta).

2. A pharmaceutical composition comprising a pharmaceutically acceptable carrier and an effective amount of the polymorphic form of claim 1.

3. A method for antagonizing the effect of substance P at its receptor site or for the blockade of neurokinin-1 receptors in a mammal which comprises the administration to the mammal of the polymorphic form of claim 1 in an amount that is effective for antagonizing the effect of substance P at its receptor site in the mammal.

4. A method for treating a condition selected from the group consisting of: diabetic neuropathy; peripheral neuropathy; AIDS related neuropathy; chemotherapy-induced neuropathy; and neuralgia, in a mammal in need thereof which comprises the administration to the mammal of an effective amount of the polymorphic form of claim 1.

5. A method for treating emesis in a mammal in need thereof which comprises the administration to the mammmal of an effective amount of the polymorphic form of claim 1.

6. A method for treating a disorder of the central nervous system in a mammal in need thereof which comprises the administration to the mammal of an effective amount of the polymorphic form of claim 1.

7. A method for treating depression in a mammal in need thereof which comprises the administration to the mammal of an effective amount of the polymorphic form of claim 1.

8. A method for treating depression in a mammal in need thereof which comprises the administration to the mammal of the polymorphic form of claim 1 and an antidepressant agent such that together they give effective relief.

9. A method for treating or preventing anxiety in a mammal in need thereof which comprises the administration to the mammal of an effective amount of the polymorphic form of claim 1.

10. A method for treating or preventing anxiety in a mammal in need thereof which comprises the administration to the mammal of the polymorphic form of claim 1 and an anti-anxiety agent such that together they give effective relief.

11. A method for treating schizophrenia in a mammal in need thereof which comprises the administration to the mammal of an effective amount of the polymorphic form of claim 1.

12. A method for treating schizophrenia in a mammal in need thereof which comprises the administration to the mammal of the polymorphic form of claim 1 and an antipsychotic agent such that together they give effective relief.

13. A process for the preparation of the polymorphic form of 2-(R)-(1-(R)-(3,5-bis(trifluoromethyl)phenyl)ethoxy)4-(5-(dimethylamino)methyl-1,2,3-triazol-4-yl)methyl-3-(S)-(4-fluorophenyl)morpholine hydrochloride of claim 1 which comprises:

adding anhydrous hydrogen chloride in isopropanol to a solution of 2-(R)-(1-(R)-(3,5-bis(tifluoromethyl)-phenyl)ethoxy)4-(5-(dimethylamino)methyl-1,2,3-triazol-4-yl)methyl-3-(S)-(4-fluorophenyl)morpholine in ethyl acetate, followed by addition of heptane to give the polymorphic form of 2-(R)-(1-(R)-(3,5-bis(trifluoromethyl)phenyl) ethoxy)-4-(5-(dimethylamino) methyl-1,2,3-triazol-4-yl)methyl-3-(S)-(4-fluorophenyl)morpholine hydrochloride of claim 1.

14. A process for the preparation of the polymorphic form of 2-(R)-(1-(R)-(3,5-bis(trifluoromethyl)phenyl)ethoxy)-4-(5-(dimethylamino) methyl-1,2,3-triazol-4-yl)methyl-3-(S)-(4-fluorophenyl)morpholine hydrochloride of claim 1 which comprises:

suspending 2-(R)-(1-(R)-(3,5-bis(trifluoromethyl)phenyl) ethoxy)-4-(5-(dimethylamino)methyl-1,2,3-triazol-4-yl)methyl-3-(S)-(4-fluorophenyl)morpholine hydrochloride of optional morphological composition in solution of ethyl acetate:isopropanol:heptane;

adding seed crystals of the polymorphic form of 2-(R)-(1-(R)-(3,5-bis(trifluoromethyl)phenyl)ethoxy)-4-(5-(dimethylamino) methyl-1,2,3-triazol-4-yl)methyl-3-(S)-(4-fluorophenyl)morpholine hydrochloride of claim 1;

stirring the resultant mixture at about 0–50° C. for a period sufficient to result in the formation of the polymorphic form of 2-(R)-(1-(R)-(3,5-bis(trifluoromethyl) phenyl)ethoxy)-4-(5-(dimethylamino) methyl-1,2,3-triazol-4-yl)methyl-3-(S)-(4-fluorophenyl)morpholine hydrochloride of claim 1.

* * * * *